United States Patent [19]

Dubroeucq et al.

[11] Patent Number: 5,633,270

[45] Date of Patent: *May 27, 1997

[54] THIAZOLIDINE DERIVATIVES, PREPARATION THEREOF AND DRUGS CONTAINING SAMEM

[75] Inventors: Marie-Christine Dubroeucq, Enghein les Bains; Franco Manfre, Limeil-Brevannes, both of France

[73] Assignee: Rhone-Poulenc Rorer S.A., Antony, France

[*] Notice: The term of this patent shall not extend beyond the expiration date of Pat. No. 5,610,144.

[21] Appl. No.: 446,745

[22] PCT Filed: Jan. 3, 1994

[86] PCT No.: PCT/FR94/00007

§ 371 Date: Jun. 6, 1995

§ 102(e) Date: Jun. 6, 1995

[87] PCT Pub. No.: WO94/15955

PCT Pub. Date: Jul. 21, 1994

[30] Foreign Application Priority Data

Jan. 7, 1993 [FR] France ..................... 93 00076

[51] Int. Cl.$^6$ ..................... C07D 277/06; A61K 31/425
[52] U.S. Cl. ............................. 514/365; 548/200

[58] Field of Search .................. 548/200; 514/365

[56] References Cited

FOREIGN PATENT DOCUMENTS

WOA9113862  9/1991  WIPO.
WOA9301167  1/1993  WIPO.

*Primary Examiner*—Robert Gerstl
*Attorney, Agent, or Firm*—Finnegan, Henderson, Farabow, Garrett & Dunner, L.L.P.

[57] ABSTRACT

Derivatives of formula (I), their salts, the preparation of said derivatives and drugs containing same. The compounds of formula (I) have interesting pharmacological properties. Said compounds have a high affinity for cholecystokinin (CCK) and gastrin receptors and are therefore useful in the treatment and prevention of CCK and gastrin-related disorders affecting the nervous system and gastrointestinal tract

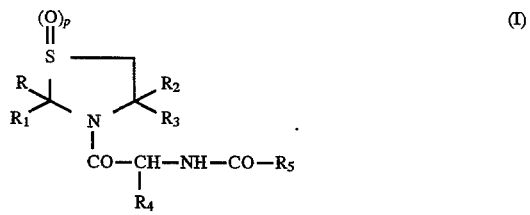

8 Claims, No Drawings

THIAZOLIDINE DERIVATIVES, PREPARATION THEREOF AND DRUGS CONTAINING SAMEM

DESCRIPTION OF THE INVENTION

The present invention relates to derivatives of formula:

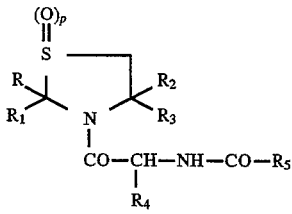

and to their salts, their preparation and medicinal products containing them.

In the formula (I):

R represents an unbranched- or branched-chain alkyl radical containing 1 to 12 carbon atoms and optionally mono- or polyunsaturated, a cycloalkyl radical containing 3 to 12 carbon atoms and optionally mono- or polyunsaturated, a polycycloalkyl radical containing 6 to 12 carbon atoms and optionally mono- or polyunsaturated, a phenylalkyl radical in which the phenyl ring is optionally substituted (with one or more substituents chosen from alkyl and alkoxy radicals or halogen atoms), a diphenylalkyl or cinnamyl radical, a pyridyl radical optionally substituted with one or more alkyl radicals, a furyl radical optionally substituted with one or more alkyl radicals, a thienyl radical optionally substituted with one or more alkyl radicals, a quinolyl radical optionally substituted with one or more alkyl radicals, a naphthyl radical optionally substituted with one or more alkyl radicals, an indolyl radical optionally substituted with one or more alkyl radicals, a 2-oxopiperidyl or quinuclidinyl radical or a phenyl radical optionally substituted with one or more substituents chosen from halogen atoms and alkyl, alkoxy, hydroxyl, nitro, amino, monoalkylamino, dialkylamino, alkoxycarbonyl, —CO—$NR_7R_8$, —NH—CO—$CH_3$, trifluoromethyl, phenyl or trifluoromethoxy radicals, $R_1$ represents a hydrogen atom, an alkyl, cycloalkyl or phenylalkyl radical or a phenyl radical optionally substituted with one or more substituents chosen from halogen atoms and alkyl and alkoxy radicals, $R_2$ represents a chain —$(CH_2)_n$—CO—$R_6$, —$(CH_2)_m$—O—CO—$R''_6$ or —$(CH_2)_m$—$NR_9R_{10}$, an oxazolinyl radical optionally substituted with one or more alkyl radicals or a 3-alkyloxadiazolyl radical, $R_3$ represents a hydrogen atom, an alkyl, cycloalkyl or phenylalkyl radical or a phenyl radical optionally substituted with one or more substituents chosen from halogen atoms and alkyl and alkoxy radicals, $R_4$ represents a hydrogen atom or an alkyl radical, $R_5$ represents a phenyl radical (optionally substituted with one or more substituents chosen from halogen atoms and alkyl, alkoxy and alkylthio radicals), a naphthyl, indolyl or quinolyl radical or a phenylamino radical in which the phenyl ring is optionally substituted with one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -—alk—O—CO—alk, —alk—COOX, —alk—O—alk, —alk'—COOX, —O—alk—COOX, —CH=CH—COOX, COOX, —alk—$SO_3$H (in salt form), —CH=CH—alk', —C(=NOH)— COOX, —S—alk—COOX, —SO—alk—COOX, —$SO_2$—alk—COOX, —O—$CH_2$—alk'—COOX, —CX=N—O—alk—COOX, —alk—N(OH)—CO—alk, —alk—$SO_2$H, —$SO_2$—NH—CO—$R_{11}$, —$SO_2$—NH—$SO_2$—$R_{11}$, —CO—NH—CO—$R_{11}$, —CO—NH—$SO_2$—$R_{11}$, —B(OH)$_2$, —C(NH$_2$)=NOH, —$SO_2$—NH—$R_{12}$, —CO—NH—$R_{12}$,

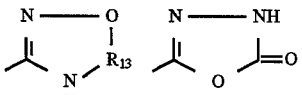

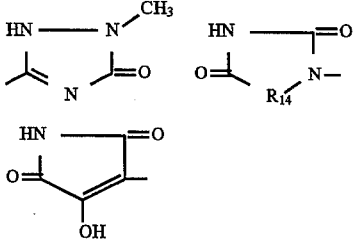

or 2,2-dimethyl-4,6-dioxo-1,3-dioxan-5-yl radicals, $R_6$ represents a hydroxyl, alkoxy, cycloalkyloxy, cycloalkylalkyloxy or phenyl radical or a radical —$NR_9R_{10}$, $R''_6$ represents an alkoxy, cycloalkyloxy, cycloalkylalkyloxy or phenyl radical or a radical —$NR_9R_{10}$, $R_7$ represents a hydrogen atom, an alkyl or phenylalkyl radical or a phenyl radical optionally substituted with one or more substituents chosen from halogen atoms and alkyl, alkoxy and alkylthio radicals, $R_8$ represents an alkyl or phenylalkyl radical or a phenyl radical optionally substituted with one or more substituents chosen from halogen atoms and alkyl, alkoxy and alkylthio radicals, or alternatively $R_7$ and $R_8$, with the nitrogen atom to which they are attached, form a saturated or unsaturated mono- or polycyclic heterocycle containing 4 to 9 carbon atoms and one or more hetero atoms (O, N) and optionally substituted with one or more alkyl radicals, $R_9$ represents a hydrogen atom, an alkyl, cycloalkylalkyl, cycloalkyl or phenylalkyl radical or a phenyl radical optionally substituted with one or more substituents chosen from halogen atoms and alkyl, alkoxy and alkylthio radicals, $R_{10}$ represents an alkyl, cycloalkylalkyl, cycloalkyl or phenylalkyl radical or a phenyl radical optionally substituted with one or more substituents chosen from halogen atoms and alkyl, alkoxy and alkylthio radicals, or alternatively $R_9$ and $R_{10}$, together with the nitrogen atom to which they are attached, form a saturated or unsaturated mono- or polycyclic heterocycle containing 4 to 9 carbon atoms and one or more hetero atoms (O, N, S) and optionally substituted with one or more alkyl radicals, $R_{11}$ represents an alkyl, cycloalkyl or trifluoromethyl radical or a phenyl radical optionally substituted with one or more substituents chosen from cyano, alkoxy, nitro and amino radicals and halogen atoms, $R_{12}$ represents a 5-tetrazolyl radical, $R_{13}$ represents C=O or S=O, $R_{14}$ represents O or C=O, p is equal to 0, 1 or 2, n is equal to 0, 1 or 2, m is equal to 1 or 2, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical, on the understanding that n is other than 0 when R and $R_3$ each represent a hydrogen atom and $R_1$ represents a pyridyl radical optionally substituted with one or more alkyl radicals, a furyl radical optionally substituted with one or more alkyl radicals, a thienyl radical optionally substituted with one or more alkyl radicals, a quinolyl radical optionally substituted with one or more alkyl radicals, a naphthyl radical optionally substituted with one or more alkyl radicals, an indolyl radical optionally substituted with one or more alkyl radicals or a phenyl radical optionally substituted with one or more substituents chosen from halogen atoms and alkyl, alkoxy, hydroxyl, nitro, amino, monoalkylamino, dialkylamino, alkoxycarbonyl, —CO—$NR_7R_8$, —NH—CO—$CH_3$, trifluoromethyl or trifluoromethoxy radicals.

In the foregoing definitions and those which will be mentioned below, except where otherwise stated, the alkyl, alkylene and alkoxy radicals and the alkyl, alkylene and alkoxy portions contain 1 to 4 carbon atoms in an unbranched or branched chain, the acyl radicals or portions contain 2 to 4 carbon atoms and the cycloalkyl radicals and portions contain 3 to 6 carbon atoms.

When R represents an unsaturated alkyl radical, the latter is preferably an isopropenyl radical.

When R represents a cycloalkyl radical, the latter is preferably a cyclohexyl radical.

When R represents an unsaturated cycloalkyl radical, the latter is preferably a tetrahydrophenyl, cyclopentadiene or dihydrophenyl radical.

When R represents a polycycloalkyl radical, the latter is preferably a norbornyl or adamantyl radical.

When R represents an unsaturated polycycloalkyl radical, the latter is preferably a norbornenyl radical.

When $R_7$ and $R_8$, with the nitrogen atom to which they are attached, form a heterocycle, the latter is preferably a piperidino ring optionally substituted with one or more alkyl radicals or a 1,2,3,4-tetrahydroquinoline ring-system.

When $R_9$ and $R_{10}$, with the nitrogen atom to which they are attached, form a heterocycle, the latter is preferably a piperidino, perhydro-1-azepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino or 1-indolinyl ring-system, it being possible for these ring-systems to be optionally substituted with at least one alk-yl radical.

The compounds of formula (I) containing one or more asymmetric centres possess isomeric forms. These isomers also form part of the invention.

The compounds of formula (I) for which p is equal to 0 and $R_5$ represents a phenylemino radical in which the phenyl ring is optionally substituted may be prepared by the action of a reactive derivative of carbamic acid, optionally obtained in situ by the action of a reactive derivative of carbonic acid chosen from N,N'-carbonyldiimidazole, phosgene, diphosgene, triphosgene and p-nitrophenylchloroformate on a derivative of formula:

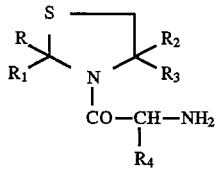
(II)

in which R, $R_1$, $R_2$, $R_3$ and $R_4$ have the same meanings as in the formula (I), on an aniline in which the phenyl ring is optionally substituted with one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH=CH—COOX, —CO—COOX, —alk—$SO_3H$, —CH=CH—alk', —C(=NOH)—COOX, —S—alk—COOX, —SO—alk—COOX, $SO_2$—alk—COOX, —O—$CH_2$—alk'—COOX, —CX=N—O—alk—COOX, —alk—N(OH)—CO—alk, 2,2-dimethyl-4,6-dioxo-1,3-dioxan-5-yl, —alk—$SO_2H$, —$SO_2$—NH—CO—$R_{11}$, —$SO_2$—NH—$SO_2$—$R_{11}$, —CO—NH—CO—$R_{11}$, —CO—NH—$SO_2$—$R_{11}$, —B(OH)$_2$, —C(NH$_2$)=NOH, —$SO_2$—NH—$R_{12}$, —CO—NH—$R_{12}$, 2,2-dimethyl-4,6-dioxo-1,3-dioxan-5-yl or

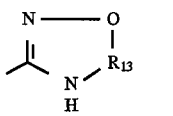

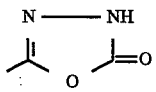

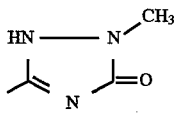

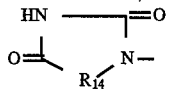

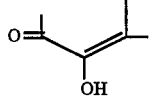

radicals.

This reaction is generally performed in an inert solvent such as tetrahydrofuran, dimethylformamide, a chlorinated solvent (for example chloroform, 1,2-dichloroethane) or an aromatic solvent (for example benzene, toluene) or a mixture of these solvents, at a temperature between 20° C. and the boiling point of the solvent.

The reactive derivative of carbamic acid may be obtained under the same solvent and temperature conditions.

The derivatives of formula (II) may be obtained by deprotection of a derivative of formula:

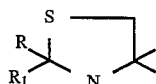
(III)

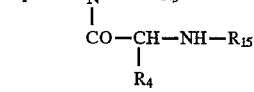

in which R, $R_1$, $R_2$, $R_3$ and $R_4$ have the same meanings as in the formula (I) and $R_{15}$ represents a protective group such as tert-butoxycarbonyl or benzyloxycarbonyl.

When $R_{15}$ represents a tert-butoxycarbonyl radical, this deprotection is preferably performed by means of iodotrimethylsilane, in an inert solvent such as a chlorinated solvent (for example chloroform, 1,2-dichloroethane), at a temperature of between 15 and 40° C. When $R_{15}$ represents a benzyloxycarbonyl radical, this deprotection is preferably performed by hydrogenation by means of hydrogen or ammonium formate, in the presence of palladium on charcoal, in an inert solvent such as ethyl acetate or methanol, at a temperature between 20° C. and the boiling point of the reaction medium.

The derivatives of formula (III) for which $R_2$ represents a chain —$(CH_2)$n—CO—$R_6$, n is equal to 0 and $R_6$ represents an alkoxy, cycloalkyloxy or cycloalkylalkyloxy radical may be obtained by the action of a derivative of formula:

in which R, $R_1$ and $R_3$ have the same meanings as in the formula (I) and $R_2$ has the same meanings as above, on an acid of formula:

in which $R_4$ is defined as in the formula (I) and $R_{15}$ is defined as in the formula (III).

This reaction is performed in an inert solvent such as acetonitrile, tetrahydrofuran or a chlorinated solvent, in the presence of a condensing agent used in peptide chemistry such as a carbodiimide (for example N,N'-dicyclohexylcarbodiimide) or an alkylchloroformate, at a temperature of between 10 and 40° C.

The derivatives of formula (V) may be obtained according to the usual methods for protection of amino acids.

The derivatives of formula (IV) for which $R_2$ represents a chain —$(CH_2)_n$—CO—$R_6$, n is equal to 0 and $R_6$ represents a hydroxyl or alkoxy radical may be obtained by the action of a derivative of formula:

in which R and $R_1$ have the same meanings as in the formula (I), on a derivative of formula:

in which $R_3$ has the same meanings as in the formula (I) and $R_6$ represents a hydroxyl or alkoxy radical, or a salt of such a compound.

This reaction is generally performed in an inert solvent such as an alcohol or a chlorinated solvent, at the boiling point of the reaction medium, optionally in the presence of a trialkylamine when the compound (VI) is in salt form, or by adaptation of the method described by J. C. SHEEMAN et al., J. Am. Chem. Soc., 80, 1158 (1958).

The derivatives of formula (VII) for which $R_3$ is not a hydrogen atom may be obtained by application or adaptation of the method described by O. W. GRIFFITH, J. Biol. Chem., 1591–1598 (1983).

The derivatives of formula (IV) for which R is not unsaturated, $R_2$ represents a chain —$(CH_2)_n$—CO—$R_6$, n is equal to 0 and R6 represents an alkoxy, cycloalkyloxy or cycloalkylalkyloxy radical may be obtained by esterification of the corresponding derivatives for which $R_6$ represents a hydroxyl radical.

This esterification is performed by means an alcohol $R_{16}$—OH in which $R_{16}$ represents an alkyl, cycloalkyl or cycloalkylalkyl radical, in an acid medium, at the boiling point of the reaction mixture.

The derivatives of formula (IV) for which R is not unsaturated and is other than benzyl or benzhydryl, $R_2$ represents a chain —$(CH_2)_n$—CO—$R_6$, n is equal to 0 and $R_6$ represents a tert-butoxy radical may be obtained by the action of isobutene on a corresponding derivative of formula (IV) for which $R_6$ represents a hydroxyl radical.

This reaction is performed in an inert solvent such as a chlorinated solvent, in the presence of an acid such as sulphuric acid, at a temperature in the region of 20° C.

The derivatives of formula (IV) for which $R_2$ represents a chain —$(CH_2)_n$—CO—$R_6$, n is equal to 0 and $R_6$ represents an alkoxy (except methoxy or ethoxy), cycloalkyloxy or cycloalkylalkyloxy radical may also be obtained by deprotection of a derivative of formula:

in which R, $R_1$ and $R_3$ have the same meanings as in the formula (IV) and $R_2$ represents a chain —$(CH_2)_n$—CO—$R_6$, n is equal to 0 and $R_6$ represents an alkoxy (except methoxy or ethoxy), cycloalkyloxy or cycloalkylalkyloxy radical.

This reaction is performed in an inert solvent such as a chlorinated solvent, by means of iodotrimethylsilane, at a temperature between 15° C. and the boiling point of the reaction medium.

The derivatives of formula (VIII) may be obtained by esterification of an acid of formula:

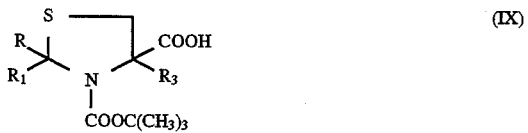

in which R, $R_1$ and $R_3$ have the same meanings as in the formula (IV).

This esterification is performed by means of an alcohol, in the presence of tosyl chloride, in pyridine, at a temperature of between 0° and 25° C.

The acids of formula (IX) may be obtained by the action of di-tert-butyl dicarbonate on a derivative of formula (IV) in which R, $R_1$ and $R_3$ have the same meanings as in the formula (IV), $R_2$ represents a chain —$(CH_2)_n$—CO—$R_6$, n is equal to 0 and $R_6$ represents a hydroxyl radical.

This reaction is performed in an inert solvent such was water, dioxane or a mixture of these solvents, in the presence of an alkali metal carbonate, at a temperature in the region of 20° C.

The derivatives of formula (III) for which $R_2$ represents a radical —$(CH_2)_m$—O—CO—$R''_6$ may be obtained by the action of a derivative of formula:

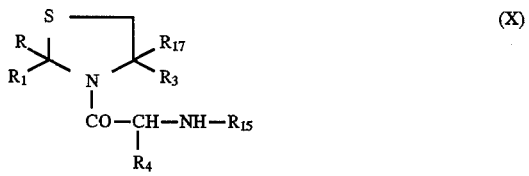

R, $R_1$ and $R_3$ have the same meanings as in the formula (III) and $R_{17}$ represents a radical —$(CH_2)_m$—OH with a halide of formula Hal—CO—$R''_6$ in which Hal represents a halogen atom, $R''_6$ has the same meanings as in the formula (I) and $R_{15}$ represents a protective group such as tert-butoxycarbonyl or benzyloxycarbonyl.

This reaction is preferably performed in an inert solvent such as a chlorinated solvent, in the presence of a trialkylamine, at a temperature in the region of 25° C., or optionally in the presence of sodium hydride in dimethylformamide at a temperature of between 0° and 25 ° C.

The derivatives of formula (X) for which $R_{17}$ represents a radical —$(CH_2)_m$—OH may be obtained from the corresponding derivatives of formula (III) for which $R_2$ represents a chain —$(CH_2)_n$—CO—$R_6$, n is equal to 0 or 1 and $R_6$ represents an alkoxy radical, according to the technique described by K. SOAI et al., Synth. Comm., 12, 463 (1982) which consists in reacting sodium borohydride with a corresponding derivative of formula (III).

This reaction is performed in an inert solvent, and preferably in a mixture of tert-butanol and methanol, at the boiling point of the reaction mixture.

The compounds of formula (III) for which $R_2$ represents a radical —$(CH_2)_m$—O—CO—$R''_6$, $R''_6$ represents a radical —$NR_9R_{10}$ and $R_9$ represents a hydrogen atom can also be obtained by reacting a compound of formula (X) in which R, $R_1$ and $R_3$ have the same meanings as in the formula (III) and $R_{17}$ represents a radical —$(CH_2)_m$—OH with an isocyanate of formula $R_{10}NCO$ in which $R_{10}$ has the same meanings as in the formula (I).

This reaction is performed in an inert solvent such as tetrahydrofuran, at a temperature in the region of 20° C., and optionally in the presence of an alkali metal methylate (for example sodium or lithium methylate).

The isocyanates are commercially available or may be obtained by application or adaptation of the methods described by R. RICHTER et al., The Chemistry of Cyanate and their thio derivatives, S. PATAI, part 2, Wiley New York (1977) and in the examples.

The derivatives of formula (III) for which $R_2$ represents a radical —$(CH_2)_m$—$NR_9R_{10}$ may be obtained by the action of an amine $HNR_9R_{10}$ in which $R_9$ and $R_{10}$ have the same meanings as in the formula (I) on a derivative of formula (X) in which $R_{17}$ represents a radical —$(CH_2)_m$—O—$SO_2$—$CH_3$.

This reaction is generally performed either in the presence of a large excess of amine, at a temperature of between 0° and 10° C., or, when the amine hydrochloride is used, in a chlorinated solvent, in the presence of a trialkylamine, at a temperature between 20° C. and the boiling point of the reaction medium.

The derivatives of formula (X) in which $R_{17}$ represents a radical —$(CH_2)_m$—O—$SO_2$—$CH_3$ may be obtained by reacting a corresponding derivative of formula (X) for which $R_{17}$ represents a radical —$(CH_2)_m$—OH with methanesulphonyl chloride.

This reaction is generally performed in an inert solvent such as acetonitrile or methylene chloride, in the presence of triethylamine, at a temperature between 0° C. and the boiling point of the reaction medium.

The derivatives of formula (III) for which R represents a radical —$(CH_2)_n$—CO—$R_6$ and $R_6$ represents an alkoxy, cycloalkoxy or cycloalkylalkyloxy radical may be obtained by esterification of the corresponding derivatives of formula (III) for which $R_2$ represents a radical —$(CH_2)_n$—CO—$R_6$ and $R_6$ represents a hydroxyl radical.

This reaction is preferably performed by means of an alcohol $R_{16}$—OH in which $R_{16}$ represents an alkyl, cycloalkyl or cycloalkylalkyl radical, in the presence of tosyl chloride, in pyridine, at a temperature of between 0° and 25° C., or, when $R_{15}$ represents a benzyloxycarbonyl radical, in an acid medium, at the boiling point of the reaction mixture.

The derivatives of formula (III) for which $R_2$ represents a radical —$(CH_2)_n$—CO—$R_6$, $R_6$ represents a hydroxyl radical, $R_{15}$ represents a benzyloxycarbonyl radical and n is equal to 1 or 2 may be obtained by hydrolysis of a derivative of formula (X) in which $R_{17}$ represents a radical —$(CH_2)_n$—CN.

This reaction is carried out by means of an acid such as sulphuric acid or hydrochloric acid, at a temperature of between 20° and 100° C.

The derivatives of formula (X) in which $R_{17}$ represents a radical —$(CH_2)_n$—CN and n is equal to 1 or 2 may be obtained by the action of potassium cyanide on a derivative of formula (X) in which $R_{17}$ represents a radical —$(CH_2)_m$—O—$SO_2$—$CH_3$.

This reaction is preferably performed in an inert solvent such as an alcohol, dimethylformamide or dimethyl sulphoxide, at a temperature of between 25° and 1000° C.

The derivatives of formula (III) for which $R_2$ represents a radical —$(CH_2)_n$—CO—$R_6$ and $R_6$ represents a phenyl radical may be obtained by the action of a corresponding derivative of formula (III) for which $R_2$ represents a radical —$(CH_2)_n$—CO—$R_6$ and $R_6$ represents an alkoxy radical with phenylmagnesium bromide.

This reaction is preferably performed in an inert solvent such as tetrahydrofuran or ethyl ether, at a temperature between −70° C. and the boiling point of the reaction mixture.

The derivatives of formula (III) for which R is not unsaturated, $R_2$ represents a radical —$(CH_2)_n$—CO—$R_6$, $R_6$ represents a phenyl radical and n is equal to 1 or 2 may also be obtained by hydrolysis of corresponding derivative of formula (X) in which $R_{17}$ represents a radical —$(CH_2)_n$—C(=NH)—$C_6H_5$ in which n is equal to 1 or 2.

This reaction is generally performed in an acid medium (for example 3N hydrochloric acid) at a temperature between 25° C. and the boiling point of the reaction medium.

The derivatives of formula (X) in which $R_{17}$ represents a radical —$(CH_2)_n$—C(=NH)—$C_6H_5$ may be obtained by the action of phenyllithium on a corresponding derivative of formula (X) in which $R_{17}$ represents a radical —$(CH_2)_n$—CN.

This reaction is performed in an inert solvent such as tetrahydrofuran or ethyl ether, at a temperature of between 0° and 25° C.

The compounds of formula (III) for which $R_2$ represents an optionally substituted oxazolinyl radical may be obtained by the action of a corresponding derivative of formula (III) for which $R_2$ represents a radical —$(CH_2)_n$—CO—$R_6$, n is equal to 0 and $R_6$ represents a hydroxyl radical, on the 2-aminoethanol optionally substituted with one or more alkyl radicals.

This reaction is performed in an inert solvent such as toluene, removing the water formed, at the boiling point of the reaction medium.

The compounds of formula (III) for which $R_2$ represents a radical —$(CH_2)_n$—CO—$R_6$, $R_6$ represents a hydroxyl radical and n is equal to 0 may be obtained by saponification of a corresponding derivative of formula (III) for which $R_6$ represents an alkoxy radical.

This reaction is performed in inert solvents such as tetrahydrofuran, methanol or dioxane and water, in the presence of a base such as sodium hydroxide, potassium hydroxide or lithium hydroxide, at a temperature of between 0° and 25° C.

The compounds of formula (III) for which $R_2$ represents a 3-alkyloxadiazolyl radical may be obtained by the action of a corresponding derivative of formula (III) for which $R_2$ represents a radical —$(CH_2)_n$—CO—$R_6$, n is equal to 0 and $R_6$ represents an alkoxy radical on an alkylamidoxime.

This reaction is performed in an inert solvent such as tetrahydrofuran, in the presence of sodium hydride, at a temperature between 25° C. and the boiling point of the reaction medium.

The derivatives of formula (III) for which $R_2$ represents a chain —$(CH_2)_n$—CO—$R_6$ and $R_6$ represents a radical —$NR_9R_{10}$ may be prepared by reacting a corresponding derivative of formula (III) in which $R_2$ represents a chain —$(CH_2)_n$—CO—$R_6$ and $R_6$ represents a hydroxyl radical, or a reactive derivative of this acid, with an amine HN—$R_9R_{10}$.

When the acid is employed, the reaction is carried out in the presence of a condensing agent used in peptide chemistry, such as a carbodiimide (for example N,N'-dicyclohexylcarbodiimide) or N,N'-carbonyldiimidazole, in an inert solvent such as an ether (for example tetrahydrofuran, dioxane), an amide (dimethylformamide) or a chlorinated solvent (for example methylene chloride, 1,2-dichloroethane, chloroform), at a temperature between 0° C. and the refluxing temperature of the reaction mixture.

When a reactive derivative of the acid is employed, it is possible to react the anhydride, a mixed anhydride or an ester (which may be chosen from activated or unactivated esters of the acid).

The reaction is then carried out either in an organic medium, optionally in the presence of an acceptor for acid such as a nitrogenous organic base (for example trialkylamine, pyridine, 1,8-diazabicyclo-[5.4.0]undec-7-ene or 1,5-diazabicyclo[4.3.0]-non-5-ene), in a solvent such as is mentioned above, or a mixture of these solvents, at a temperature between 0° C. and the refluxing temperature of the reaction mixture, or in a two-phase aqueous-organic medium in the presence of an alkali metal base or alkaline-earth metal base (sodium hydroxide, potassium hydroxide) or an alkali metal carbonate or bicarbonate or alkaline-earth metal carbonate or bicarbonate, at a temperature of between 0° and 40° C.

The anilines, where appropriate substituted, are commercially available or may be obtained by application or adaptation of the methods described by R. SCHRÖTER, Methoden der organischen Chemie, Houben Weil, Band XI/1, p 360; G. J. ESSELEN et al., J. Am. Chem. Soc., 36, 322 (1914); G. ADRIANT et al., Bull. Soc. Chim. FR, 1511 (1970); W. A. JACOBS et al., J. Am. Chem. Soc., 39, 2418 (1917) and J. Am. Chem. Soc., 39, 1435 (1917), and in the examples.

The compounds of formula (I) for which p is equal to 0 and $R_5$ represents a phenylamino radical in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O—CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk'—COOX, —CX=N—O—alk—COOX, —alk—COOX or —alk'—COOX radicals in which X is other than a hydrogen atom may also be prepared by the action of a derivative of formula (II) on a phenyl isocyanate in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O—CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk'—COOX, —CX=N—O—alk—COOX, —alk—COOX or —alk'—COOX radicals in which X is other than a hydrogen atom.

This reaction is generally performed in an inert solvent such as tetrahydrofuran, dimethylformamide, a chlorinated solvent (for example chloroform, 1,2-dichloroethane) or an aromatic solvent (for example benzene, toluene), at a temperature between 10° C. and the boiling point of the solvent.

The phenyl isocyanates are commercially available or may be obtained by application or adaptation of the methods described by R. RICHTER et al., The Chemistry of Cyanate and their thio derivatives, S. PATAI, part 2, Wiley New York (1977) and in the examples.

The compounds of formula (I) for which p is equal to 0 and $R_5$ represents an optionally substituted phenyl radical or a naphthyl, indolyl or quinolyl radical may be prepared by the action of a derivative of formula (II) on an acid of formula HOOC—$R_5$ in which $R_5$ has the same meanings as above, or a reactive derivative of this acid.

When the acid is employed, the reaction is carried out in the presence of a condensing agent used in peptide chemistry, such as a carbodiimide (for example N,N'-dicyclohexylcarbodiimide) or N,N'-carbonyldiimidazole, in an inert solvent such as an ether (for example tetrahydrofuran, dioxane), an amide (dimethylformamide) or a chlorinated solvent (for example methylene chloride, 1,2-dichloroethane, chloroform), at a temperature between 0° C. and the refluxing temperature of the reaction mixture.

When a reactive derivative of the acid is employed, it is possible to react the anhydride, a mixed anhydride or an ester (which may be chosen from activated or unactivated esters of the acid).

The reaction is then carried out either in an organic medium, optionally in the presence of an acceptor for acid such as a nitrogenous organic base (for example trialkylamine, pyridine, 1,8-diazabicyclo-[5.4.0]undec-7-ene or 1,5-diazabicyclo[4.3.0]-non-5-ene), in a solvent such as is mentioned above, or a mixture of these solvents, at a temperature between 0° C. and the refluxing temperature of the reaction mixture, or in a two-phase aqueous-organic medium in the presence of an alkali metal base (sodium hydroxide, potassium hydroxide) or alkaline-earth metal base or an alkali metal carbonate or bicarbonate or alkaline-earth metal carbonate or bicarbonate, at a temperature of between 0° and 40° C.

The compounds of formula (I) [or which p is equal to 0 and $R_5$ represents a phenylamino radical in which the phenyl ring is substituted with a carboxyl, —alk—COOH, O—alk—COOH, —alk'—COOH, —CH=CH—COOH, —CO—COOH, —S—alk—COOH, —SO—alk—COOH, —$SO_2$—alk—COOH, —C(=NOH)—COOH, —O—CH2—alk,—COOH or —CX=N—O—alk—COOH radical and/or $R_2$ represents a chain —$(CH_2)_n$—COOH may also be prepared by hydrolysis or, depending on the case, hydrogenolysis of the corresponding esters of formula (I).

When alkyl or phenylalkyl esters are used, it is advantageous to perform the hydrolysis by means of a base such as sodium hydroxide, potassium hydroxide, or lithium hydroxide, in an inert solvent such as tetrahydrofuran, methanol, dioxane, water or a mixture of these solvents, at a temperature of between 20° C. and 40° C. When a trimethylsilylethyl ester is used, it is advantageous to work in an inert solvent such as tetrahydrofuran, by means of a fluoride such as tetrabutylammonium fluoride, at a temperature of between 10° and 40° C. When phenylalkyl esters are used, it is possibly also advantageous to perform a hydrogenolysis by means of hydrogen or ammonium formate in the presence of a catalyst such as palladium on charcoal in a solvent such as methanol or ethyl acetate. When tert-butyl esters are used, it is advantageous to perform the hydrolysis by means of an acid such as trifluoroacetic acid.

The trimethylsilylethyl esters may be obtained by application or adaptation of the method described by H. GERLACH, Helv. Chim. Acta, 60, 3039 (1977).

The compounds of formula (I) for which p is equal to 0 and $R_5$ represents a phenylamino radical in which the phenyl ring is substituted with a hydroxyiminoalkyl or alkoxyiminoalkyl radical may also be prepared by the action of the corresponding acylated derivative of formula (I) on a derivative of formula:

$$H_2N—OR_{18} \qquad (XI)$$

in which $R_{18}$ represents a hydrogen atom or an alkyl radical.

This reaction is generally performed in an inert solvent such as an alcohol (for example methanol, ethanol), water or a mixture of these solvents, at the boiling point of the solvent and optionally in the presence of a base such as pyridine.

The compounds of formula (I) for which p is equal to 0, $R_2$ represents a chain —$(CH_2)_n$—CO—$R_6$, n is equal to 0, $R_6$ represents an alkoxy, cycloalkyloxy or cycloalkylalkyloxy radical and $R_5$ represents an optionally substituted phenyl radical, a naphthyl, indolyl or quinolyl radical or a phenylamino radical in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, —alk—O—CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk'—COOX, —CX=N—O—alk—COOX, —alk—COOX or —alk'—COOX radicals in which X is other than a hydrogen atom may also be prepared by the action of a derivative of formula (IV) on an acid of formula:

$$\underset{\underset{R_4}{|}}{HOOC—CH—NH—CO—R_5} \qquad (XII)$$

in which $R_5$ has the same meanings as above, or a reactive derivative of this acid, and $R_4$ has the same meanings as in the formula (I).

This reaction is preferably performed in the presence of a condensing agent used in peptide chemistry such as a carbodiimide, in a solvent such as acetonitrile, tetrahydrofuran or a chlorinated solvent, or by means of thionyl chloride in dichloromethane at a temperature between 10° C. and the boiling point of the solvent.

The acids of formula (XII) may be obtained by application or adaptation of the method described by J. R. JOHNSON et al., J. Am. Chem. Soc., 69, 2370 (1947) or, for the compounds for which $R_5$ represents a phenylamino radical in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, trifluoromethylsulphonamido, carbamoyl, alkoxyiminoalkyl, alkoxyaminocarbonyl, —alk—O—CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk'—COOX, —CX=N—O—alk—COOX, —alk—COOX or —alk'—COOX radicals in which X is other than a hydrogen atom, by the action of a phenyl isocyanate in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, trifluoromethylsulphonamido, carbamoyl, alkoxyiminoalkyl, alkoxyaminocarbonyl, —alk—O—CO—alk, —CH=CH—alk', —alk—O—alk, trifluoromethylsulphonamido, —alk—$SO_3H$ (in salt form), —O—alk—COOX, —CH=CH—COOX, —CO—COOX, —S—alk—COOX, —SO—alk—COOX, —$SO_2$—alk—COOX, —O—$CH_2$—alk,—COOX, —CX=N—O—alk—COOX, —alk—COOX or —alk'—COOX radicals in which X is other than a hydrogen atom on a derivative of formula:

$$\underset{\underset{R_4}{|}}{HOOC—CH—NH_2} \qquad (XIII)$$

in which $R_4$ has the same meanings as in the formula (I).

This reaction is generally performed in aqueous solution in the presence of a base such as an alkali metal bicarbonate or in aqueous dioxane, at a temperature in the region of 20° C.

The compounds of formula (I) for which p is equal to 0 and R represents a saturated cycloalkyl radical or a saturated polycycloalkyl radical may be prepared by hydrogenation of a corresponding unsaturated derivative of formula (I).

This reaction is performed by means of hydrogen or ammonium formate, in the presence of a catalyst such as palladium on charcoal, in an inert solvent such as methanol or ethyl acetate, at a temperature between 25° C. and the boiling point of the reaction medium.

The compounds of formula (I) for which p is equal to 1 or 2 may be prepared by oxidation of the corresponding compounds of formula (I) for which p is equal to 0, on the understanding that the other radicals and other substituents are chosen in such a way as to be insensitive to the conditions of the reaction.

This oxidation is generally performed by means of Oxone$^R$ (potassium peroxymonosulphate) marketed by Aldrich, in an alcohol such as methanol or a methanol/water mixture, at a temperature in the region of 25° C.

For a person skilled in the art, it is understood that, [lacuna] carrying out the processes according to the invention described above, it may be necessary, in order to avoid side reactions, to introduce groups protecting the amine, alcohol, acid or ketone functions, such as those described by T. W. GREENE, Protective groups in organic synthesis, John Wiley and Sons, New York. For example, the amine functions may be blocked in the form of tert-butyl or methylcarbamates and then regenerated by means of iodotrimethylsilane or in the form of benzylcarbamates and then regenerated by hydrogenation after the process according to the invention has been carried out. The alcohol functions can, for example, be blocked in the form of a benzoate and then regenerated by hydrolysis in an alkaline medium after the process according to the invention has been carried out. The ketone functions may be blocked in the form of a 1,3-dioxolane and then regenerated by means of of a hydrochloric acid/acetic acid mixture.

The enentiomers of the compounds of formula (I) containing at least one asymmetric site may be obtained by resolution of the racemates, for example by chromatography on a chiral column, or by synthesis from chiral precursors.

The compounds of formula (I) may be purified by the usual known methods, for example by crystallization, chromatography or extractions.

The compounds of formula (I) containing a basic residue can be optionally converted to addition salts with an inorganic or organic acid, by the action of such an acid in an organic solvent such as an alcohol, a ketone, an ether or a chlorinated solvent.

The compounds of formula (I) containing an acid residue can be optionally converted to metal salts or to addition salts with nitrogenous bases according to methods known per se. These salts may be obtained by the action of a metal-containing base (for example containing an alkali metal or alkaline-earth metal), ammonia, an amine or an amine salt on a compound of formula (I), in a solvent. The salt formed is separated by the usual methods.

These salts also form part of the invention.

As examples of pharmaceutically acceptable salts, there may be mentioned the addition salts with inorganic or organic acids (such as acetate, propionate, succinate, benzoate, fumarate, maleate, oxalate, methanesulphonate, isethionate, theophyllineacetate, salicylate, methylene-bis (β-hydroxynaphthoate, hydrochloride, sulphate, nitrate and phosphate), the salts with alkali metals (sodium, potassium, lithium) or with alkaline-earth metals (calcium, magnesium), the ammonium salts and the salts of nitrogenous bases (ethanolamine, trimethylamine, methylamine, benzylamine, N-benzyl-β-phenethylamine, choline, arginine, leucine, lysine, N-methylglucamine).

The compounds of formula (I) exhibit advantageous pharmacological properties. These compounds possess a strong affinity for cholecystokinin (CCK) receptors and gastrin receptors, and are hence useful in the treatment and prevention of disorders linked to CCK and to gastrin affecting the nervous system and the gastrointestinal system.

Thus, these compounds may be used for the treatment or prevention of psychoses, anxiety disorders, depression, neurodegeneration, panic attacks, Parkinson's disease, tardive dyskinesia, irritable colon syndrome, acute pancreatitis, ulcers, disorders of intestinal motility and certain CCK-sensitive tumours, as an appetite regulator, in the withdrawal of chronic treatments and abuse of alcohol and of medicinal products and as a constrictor of the pupil of the eye.

These compounds also have a potentiating effect on the analgesic activity of narcotic and non-narcotic medicinal products. In addition, they can have an analgesic effect of their own.

Moreover, compounds having a strong affinity for CCK receptors modify the capacity for memorization. Consequently these compounds may be effective in memory disorders.

The affinity of the compounds of formula (I) for CCK receptors was determined according to a technique based on that of A. SAITO et al. (J. Neuro. Chem., 37, 483–490 (1981)), in the cerebral cortex and in the pancreas.

In these tests, the $IC_{50}$ of the compounds of formula (I) is generally less than or equal to 1000 nM.

Moreover, it is known that products which recognise the central CCK receptors have a similar specificity for the gastrin receptors in the gastrointestinal tract (BOCK et al., J. Med. Chem., 32, 16–23 (1989); REYFELD et al., Am. J. Physiol., 240, G255–266 (1981); BEINFELD et al., Neuropeptides, 3, 411–427 (1983)).

The compounds of formula (I) exhibit low toxicity. Their $LD_{50}$ is generally greater than 40 mg/kg via the subcutaneous route in mice.

Preferred compounds of formula (I) are those for which R represents an unbranched- or branched-chain alkyl radical containing 1 to 12 carbon atoms, a cycloalkyl radical containing 3 to 12 carbon atoms and optionally monounsaturated, a polycycloalkyl radical containing 6 to 12 carbon atoms and optionally mono- or polyunsaturated, a phenylalkyl radical or a phenyl radical optionally substituted with one or more substituents chosen from halogen atoms and alkyl, —alk—COOX and carboxyl radicals, $R_1$ represents a hydrogen atom, $R_2$ represents a chain —$(CH_2)_n$—CO—$R_6$, $R_3$ represents a hydrogen atom, $R_4$ represents a hydrogen atom and $R_5$ represents a phenylamino radical in which the phenyl ring is substituted with an alkyl, —alk—COOX or carboxyl radical.

Of special importance are the following compounds:
(4R)-3-{3-[2-(4-tert-Butoxycarbonyl-2-cyclohexyl-3-thiazolidinyl)-2-oxo ethyl]ureido}phenylacetic acid,
tert-Butyl (4R)-3-{2-[3-(3-methylphenyl)ureido]-acetyl}-2-benzyl-4-thiazolidinecarboxylate,
(4R)-3-{3-[2-(4-tert-Butoxycarbonyl-2-benzyl-3-thiazolidinyl)-2-oxoethyl]ureido}phenylacetic acid,
(2R, 4R)-3-[3-{2-[4-tert-Butoxycarbonyl-2-((RS)-1,2,3,6-tetrahydro-1-phenol)-3-thiazolidinyl]-2-oxoethyl}ureido] phenolacetic acid,
(4R)—3-[3-{2-[4-tert-Butoxycarbonyl-2-[(2RS)-5-norbornen-2-yl]-3-thiazolidinyl]-2-oxoethyl}ureido]-phenolacetic acid,
Methyl (4R)-3-[3-{2-[4-tert-butoxycarbonyl-2-[(2RS)-5-norbornen-2-yl]-3-thiazolidinyl]-2-oxoethyl}ureido]-phenylacetate,
(4R)-3-[3-{2-[4-tert-Butoxycarbonyl-2- [(2RS)-5-norbornen-2-yl]-3-thiazolidinyl]-2-oxoethyl}ureido]-phenylacetic acid,
(4R)-3-[3-{2-[4-tert-Butoxycarbonyl-2-((2RS)-2-norbornyl)-3-thiazolidinyl]-2-oxoethyl}-ureido]-phenylacetic acid,
tert-Butyl (4R) -3-{2-[3-(3-methylphenyl)ureido]-acetyl}-2-[(RS)-5-norbornen-2-yl]thiazolidinecarbonlate,
(4R)-3-{3-2-(4-tert-Butoxycarbonyl-2-tert-butyl-3-thiazolidinyl)-2-oxoethyl]ureido)phenylacetic acid,
(S)-3-{3-[2-((4R)-4-tert-butoxycarbonyl-2-butyl-3-thiazolidinyl]- 2-oxoethyl]ureido}-2-phenylpropionic acid,
tert-Butyl (4R) -3-{2-[3-(3-methylphenyl)ureido]-acetyl}-2-butyl-4-thiazolidinecarboxylate,
(4R)-3-{3-[2-(4-tert-Butoxycarbonyl-2-butyl-3-thiazolidinyl)-2-oxoethyl]ureido}benzoic acid,
tert-Butyl (2R, 4R) -3- {2-[3-(3-methylphenyl)ureido]-acetyl}-2-((RS)-1,2,3,6-tetrahydro-1-phenyl)-4-thiazolidinecarboxylate,
(2R, 4R)-3-[3-{2-[4-tert-Butoxycarbonyl-2-(2-phenylphenyl)-3-thiazolidinyl]-2-oxoethyl}ureido]-phenylacetic acid,
tert-Butyl (2R, 4R)-3-{2-[3-(3-methylphenyl)ureido]-acetyl}-2-(2-phenylphenyl )-4-thiazolidinecarboxylate,
(S)-3-[[3-{2-[(2R,4RS)-4-Carboxy-1-2-(2-fluorophenyl)-3-thiazolidinyl]-2-oxoethyl}ureido]-2-phenylpropionic acid, their isomers, the mixtures of their isomers and their salts.

EXAMPLES

The examples which follow illustrate the invention without limiting it.

EXAMPLE 1

30 cm³ of methanol are added slowly under an inert atmosphere into a round-bottomed flask containing 2.0 g of benzyl (4R) -3-{3- [2- (4-tert-butoxycarbonyl-2-cyclohexyl-3-thiazolidinyl)-2-oxoethyl]-ureido}phenyl-acetate (isomer A), 1.7 g of ammonium formate and 2.0 g of palladium on charcoal (10% Pd). The reaction medium is heated to reflux for 2 hours and then cooled to a temperature in the region of 25° C. The catalyst is separated by filtration and the filtrate is concentrated to dryness under reduced pressure at 40° C. The residue obtained is dissolved in 25 cm³ of 0.1N aqueous sodium hydroxide solution and washed with twice 10 cm³ of diethyl ether. The aqueous phase is brought to pH 2 by adding 1N aqueous sulphuric acid solution. The precipitated product is separated by filtration, washed with twice 10 cm³ of water and dried in the air. 1.0 g of (4R) -3-{3- [2-(4-tert-butoxycarbonyl-2-cyclohexyl-3-thiazolidinyl)-2-oxoethyl]ureido}phenylacetic acid (isomer A), melting point 115° C., is thereby obtained; $[\alpha]_D^{25} = -32.9° \pm 1.2°$ (C %=1.2; DMF).

NMR (200 MHz, δ in ppm, DMSO-$d_6$+2 drops of $CD_3COOD$). A mixture of two rotamers is observed in the proportions 75:25. 0.70 to 2.00 (mt, 11H, —CH— and —CH$_2$— of cyclohexyl), 1.38 and 1.47 (2s, 9H in total, —C(CH$_3$)$_3$), 3.34 (d, J=6.5 Hz, S—CH$_2$— of the preponderant rotamer), 3.07 and 3.49 (2 mt, —S—CH$_2$— of the less abundant rotamer), 3.47 (s, 2H, Ar—CH$_2$—COO—), 4.00 and 4.10 (2 AB, J=17.0 Hz, 2H, N—CH$_2$—CO—), 4.69 (t, J=8.5 Hz, N—CH—CO— of the less abundant rotamer), 5.03 (d, J=9.0 Hz, —N—CH—S of the less abundant rotamer), 5.09 (t, J=6.5 Hz, N—CH—CO— of the preponderant rotamer), 5.24 (d, J=9.5 Hz, N—CH—S of the preponderant rotamer), 6.78 (d, J=8.0 Hz), H at position 4 of Ar—NH—CO— of the preponderant rotamer), 6.86 (d, J=8.0 Hz, H at position 4 of Ar—NH—CO— of the less abundant rotamer), 7.15 (t, J=8.0 Hz, 1H, H at position 5 of Ar—NH—CO—), 7.15 to 7.45 (mt, 2H of Ar—NH—CO—).

<u>A</u> Benzyl (4R)-3-{3-[2-(4-tert-butoxycarbonyl-2-cyclohexyl-3-thiazolidinyl)-2-oxoethyl]ureido}-phenylacetate (isomer A) may be prepared in the following manner: 1.1 g of benzol 3-isocyanatophenylacetate dissolved in 10 cm³ of chloroform are added at a temperature in the region of 25° C. to a solution of 1.38 g of tert-butyl (4R)-3-(2-aminoacetyl)-2-cyclohexyl-4-thiazolidinecarboxylate (isomer A) in 25 cm³ of chloroform. The reaction mixture is stirred for 12 hours at a temperature in the region of 25° C. and then concentrated to dryness under reduced pressure at 35° C. The crude product obtained is purified by chromatography on silica [eluent: ethyl acetate/cyclohexane (40:60 by volume)]. The fractions containing the expected product are pooled and concentrated to dryness under reduced pressure at 40° C. 2.1 g of benzyl (4R)-3-{3-[2-(4-tert-butoxycarbonyl-2-cyclohexyl-3-thiazolidinyl)-2-oxoethyl]ureido}phenylacetate (isomer A) are thereby obtained in the form of a yellow oil, which is used in the subsequent syntheses without further treatment.

<u>B</u> tert-Butyl (4R) -3- (2-aminoacetyl) -2-cyclohexyl-4-thiazolidinecarboxylate (isomer A) may be prepared in the following manner: 0.8 cm³ of iodotrimethylsilane is added dropwise at a temperature in the region of 25° C. to a solution of 2.14 g of tert-butyl (4R)-3-(2-tert-butoxycarbonylaminoacetyl)-2-cyclohexyl-4-thiazolidinecarboxylate (isomer A) in 25 cm³ of chloroform. The reaction medium is stirred for 3 hours at a temperature in the region of 25° C., and 50 cm³ of water are then added. The aqueous phase is separated after settling has taken place and extracted with twice 10 cm³ of chloroform. The combined organic phases are washed successively with 50 cm³ of water, 50 cm³ of saturated aqueous sodium hydrogen carbonate solution and 50 cm³ of saturated aqueous sodium chloride solution, then dried over magnesium sulphate and concentrated to dryness under reduced pressure at 40° C. 1.38 g of tert-butyl (4R)-3-(2-aminoacetyl)-2-cyclohexyl-4-thiazolidinecarboxylate (isomer A) are thereby obtained in the form of a yellow oil, which is used in the subsequent syntheses without further treatment.

<u>C</u> tert-Butyl (4R)-3-(2-tert-butoxycarbonylaminoacetyl)-2-cyclohexyl-4-thiazolidinecarboxylate (isomer A) may be prepared in the following manner: a solution of 8.0 g of N,N'-dicyclohexylcarbodiimide in 75 cm³ of tetrahydrofuran is added in the course of 30 minutes to a solution of 10.6 g of tert-butyl (2RS,4R)-2-cyclohexyl-4-thiazolidinecarboxylate and 6.8 g of 2-tert-butoxycarbonylaminoacetic acid in 100 cm³ of tetrahydrofuran maintained at a temperature in the region of 0° C. The reaction medium is brought to a temperature in the region of 25° C. and is then stirred for 16 hours. The insoluble product is separated by filtration and washed with 3 times 20 cm³ of acetonitrile. The filtrate is concentrated to dryness under reduced pressure at 40° C. The crude product obtained is purified by chromatography on silica [eluent: methylene chloride/methanol (98:2 by volume)]. The fractions containing the expected product are pooled and concentrated to dryness under reduced pressure at 40° C. 9.7 g of tert-butyl (4R)-3-(2-tert-butoxycarbonylaminoacetyl)-2-cyclohexyl-4-thiazolidinecarboxylate (isomer A) are thereby obtained in the form of a yellow oil, which is used in the subsequent syntheses without further treatment.

<u>D</u> tert-Butyl (2RS,4R)-2-cyclohexyl-4-thiazolidinecarboxylate may be prepared in the following manner: 3.0 cm³ of concentrated sulphuric acid are added dropwise to a suspension, cooled to a temperature in the region of 5° C., of 12.4 g of (2RS,4R)-2-cyclohexyl-4-thiazolidinecarboxylic acid in 125 cm³ of chloroform. The reaction medium is saturated with isobutene for 2 hours while the temperature of the reaction medium is maintained in the vicinity of 5° C. After return to a temperature in the region of 20° C., stirring is continued for 12 hours. The reaction medium is treated with 200 cm³ of saturated aqueous sodium hydrogen carbonate solution. The organic phase is separated after settling has taken place and the aqueous phase is extracted with twice 100 cm³ of chloroform. The combined organic phases are washed with 100 cm³ of water and with 100 cm³ of saturated aqueous sodium chloride solution, dried over magnesium sulphate and concentrated to dryness under reduced pressure at 40° C. 10.6 g of tert-butyl (2RS,4R)-2-cyclohexyl-4-thiazolidinecarboxylate are thereby obtained in the form of a yellow oil, which is used in the subsequent syntheses without further treatment.

<u>E</u> (2RS,4R)-2-Cyclohexyl-4-thiazolidinecarboxylic acid may be prepared in the following manner: 7.0 g of cyclohexylcarboxaldehyde are added at a temperature in the region of 50° C. to a suspension of 7.26 g of L-cysteine in 100 cm³ of ethanol. The reaction medium is heated to reflux for 3 hours. After cooling to a temperature in the region of 25° C., the insoluble product is separated by filtration and washed successively with twice 50 cm³ of ethanol and twice 50 cm³ of diethyl ether. 12.4 g of (2RS,4R)-2-cyclohexyl-4-thiazolidinecarboxylic acid, melting point 248° C., are thereby obtained.

<u>F</u> Benzyl 3-isocyanatophenylacetate may be prepared in the following manner: a solution of 5.0 g of benzyl 3-aminophenylacetate in 40 cm³ of toluene is added in the course of 15 minutes at a temperature in the region of -30° C. to a suspension of 0.5 g of charcoal in a mixture of 2.6 cm³ of trichloromethyl chloroformate and 75 cm³ of toluene. The reaction mixture is stirred for 2 hours at a temperature in the region of 20° C. and then heated to reflux for 3 hours. After cooling to a temperature in the region of 25° C., the reaction medium is outgassed by bubbling nitrogen through it; the catalyst is separated by filtration and the filtrate is concentrated to dryness under reduced pressure at 40° C. 6.0 g of benzyl 3-isocyanatophenylacetate are thereby obtained in the form of a yellow oil, which is used in the subsequent syntheses without further treatment.

G Benzyl 3-aminophenylacetate may be prepared in the following manner: 265 g of ammonium chloride and 130 g of powdered zinc are added to a mixture of 28 g of benzyl 3-nitrophenylacetate in 125 cm³ of methanol and 1300 cm³ of water. The reaction medium is heated to reflux for 1 hour and then cooled to a temperature in the region of 10° C. The insoluble salts are separated by filtration and the filtrate is extracted with 3 times 500 cm³ of diethyl ether. The collected organic phases are washed successively with 100 cm³ of water and 200 cm³ of saturated aqueous sodium chloride solution. After drying over magnesium sulphate and concentration to dryness under reduced pressure, 20.5 g of benzyl 3-aminophenylacetate are thereby obtained in the form of a yellow oil, which is used in the subsequent syntheses without further treatment.

H Benzyl 3-nitrophenylacetate may be prepared in the following manner: 10.3 cm³ of oxalyl dichloride are added slowly to a mixture containing 21.0 g of 3-nitrophenylacetic acid and 0.5 cm³ of dimethylformamide in 200 cm³ of 1,2-dichloroethane. The reaction medium is stirred for 3 hours at a temperature in the region of 25° C., and 12.5 g of benzyl alcohol are then added. Stirring is continued for 12 hours at this same temperature, and the reaction medium is then washed successively with twice 100 cm³ of saturated aqueous sodium hydrogen carbonate solution, 100 cm³ of water and 100 cm³ of saturated aqueous sodium chloride solution. The collected organic phase is dried over magnesium sulphate and concentrated to dryness under reduced pressure at 40° C. The residue obtained is purified by chromatography on silica [eluent: ethyl acetate/cyclohexane (30:70 by volume)]. The fractions containing the expected product are pooled and concentrated to dryness under reduced pressure at 40° C. 28.0 g of benzyl 3-nitrophenylacetate are thereby obtained in the form of a yellow oil, which is used in the subsequent syntheses without further treatment.

EXAMPLE 2

The procedure is similar to that described in Example 1A, but starting with 3.4 g of tert-butyl (4R)-3-(2-aminoacetyl)-2-benzyl-4-thiazolidinecarboxalate (isomer A) and 1.3 g of 3-methylphenyl isocyanate. The crude product obtained is purified by chromatography on silica [eluent: ethyl acetate/cyclohexane (30:70 by volume)]. The fractions containing the expected product are pooled and concentrated to dryness under reduced pressure at 40° C. After crystallization in diethyl ether, 0.34 g of tert-butyl (4R) -3-{2-[3-(3-methylphenyl)-ureido]acetyl}-2-benzyl-4-thiazolidinecarboxylate (isomer A), melting point 104° C., is thereby obtained; $[\alpha]_D^{25} = -107.3° \pm 1.5°$ (C %=0.61; CH$_3$OH).

NMR (250 MHz, δ in ppm, DMSO-d$_6$, 403K). 1.55 (1s, 9H, —C(CH$_3$)$_3$), 2.29 (s, 3H, Ar—CH$_3$), 2.90 (dd, J=14.0 and 8.5 Hz, 1H, 1H of Ph—CH$_2$), 3.38 (d, J=7.0 Hz, 2H, S—CH$_2$—), 3.53 (dd, J=14.0 and 4.0 Hz, 1H, 1H of Ph—CH$_2$), 3.95 and 4.05 (2dd, J=17.5 Hz and 5.0 Hz, 2H, N—CH$_2$—CO—), 5.02 (t, J=7.0 Hz, 1H, —N—CH—CO—), 5.52 (dd, J=8.5 Hz and 4.0 Hz, 1H, N—CH—S—), 6.24 (t, J=5.0 Hz, 1H, —NH—CO—), 6.77 (d, J=8.0 Hz, 1H, H at position 4 of Ar—NH—CO), 7.13 (t, J=8.0 Hz, 1H, H at position 5 of Ar—NH—CO—), 7.15 to 7.40 (mt, 7H, Ph of benzyl and 2H of Ar—NH—CO—), 8.38 (broad s, 1H, H of —CO—NH—Ar).

A tert-Butyl (4R) -3- (2-aminoacetyl)-2-benzyl-4-thiazolidinecarboxylate (isomer A) may be prepared in a manner similar to that described in Example 1B, but starting with 8.50 g of tert-butyl (4R)-3-(2-tert-butoxycarbonylaminoacetyl)-2-benzyl-4-thiazolidinecarboxylate (isomer A) and 2.84 cm³ of iodotrimethyl-silane. 6.3 g of tert-butyl (4R)-3-(2-aminoacetyl)-2-benzyl-4-thiazolidinecarboxylate (isomer A) are thereby obtained in the form of a yellow oil, which is used in the subsequent syntheses without further treatment.

B tert-Butyl (4R)-3-(2-tert-butoxycarbonylaminoacetyl)-2-benzyl-4-thiazolidinecarboxylate (isomer A) may be prepared in a manner similar to that described in Example 1C, but starting with 25.7 g of tert-butyl (2RS,4R)-2-benzyl-4-thiazolidinecarboxylate, 13.9 g of 2-tert-butoxycarbonylaminoacetic acid and 16.3 g of N,N'-dicyclohexylcarbodiimide. The crude product is purified by chromatography on silica [eluent: methylene chloride/methanol (99:1 by volume)]. The fractions containing the expected product are pooled and concentrated to dryness under reduced pressure at 40° C. 12.1 g of tert-butyl (4R)-3-(2-tert-butoxycarbonyl-aminoacetyl)-2-benzyl-4-thiazolidinecarboxylate (isomer A) are thereby obtained in the form of a cream-coloured foam, which is used in the subsequent syntheses without further treatment.

C tert-Butyl (2RS,4R)-2-benzyl-4-thiazolidinecarboxalate may be prepared in the following 11.8 cm³ of iodotrimethylsilane are introduced slowly at a temperature in the region of 25° C. into a solution of 30.5 g of tert-butyl (4R)-3-tert-butoxycarbonyl-2-benzyl-4-thiazolidine-carboxylate (isomer A) in 250 cm3 of chloroform. The reaction mixture is stirred for 1 hour, and 10 cm³ of water are then added. The organic phase is separated and the aqueous phase is extracted with twice 20 cm³ of methylene chloride. The combined organic phases are washed with 100 cm³ of water and with 100 cm³ of saturated aqueous sodium hydrogen carbonate solution, dried over magnesium sulphate and concentrated to dryness under reduced pressure at 40° C. 25.0 g of tert-butyl (2RS,4R)-2-benzyl-4-thiazolidinecarboxylate are thereby obtained in the form of a yellow oil, which is used in the subsequent syntheses without further treatment.

D tert-Butyl (4R)-3-tert-butoxycarbonyl-2-benzyl-4-thiazolidinecarboxylate (isomer A) may be prepared in the following manner: 11.6 g of tert-butanol are added to a solution, cooled to a temperature in the region of 5° C., of (4R)-3-tert-butoxycarbonyl-2-benzyl-4-thiazolidinecarboxylic acid (isomer A) and 29.5 g of para-toluenesulphonyl chloride in 230 cm³ of pyridine. After return to a temperature in the region of 25° C., the reaction medium is stirred for 20 hours and then concentrated under reduced pressure at 50° C. The residue is taken up in 100 cm³ of water and extracted with 3 times 150 cm³ of ethyl acetate. The combined organic phases are washed successively with 100 cm³ of water, 100 cm³ of saturated aqueous sodium hydrogen carbonate solution, 100 cm³ of water and 100 cm³ of saturated aqueous sodium chloride solution; and then dried over magnesium sulphate and concentrated to dryness under reduced pressure. The crude product obtained is purified by chromatography on silica [eluent: ethyl acetate/cyclohexane (50:50 by volume)]. The fractions containing the expected product are pooled and concentrated to dryness under reduced pressure at 40° C. 30.0 g of tert-butyl (4R)-3-tert-butoxycarbonyl-2-benzyl-4-thiazolidinecarboxylate (isomer A) are thereby obtained in the form of an orange-coloured oil, which is used in the subsequent syntheses without further treatment.

E (4R)-3-tert-Butoxycarbonyl-2-benzyl-4-thiazolidinecarboxylic acid (isomer A) may be prepared in the following manner: a solution of 39.4 g of di-tert-butyl dicarbonate in 40 cm³ of dioxane is added at a temperature in the region of 5° C. to a solution of 40.0 g of (2RS,4R)-2-benzyl-4-thiazolidinecarboxylic acid in 360 cm³ of 0.5N aqueous sodium hydroxide solution and 230 cm³ of dioxane. After return to a temperature in the region of 25° C., the reaction mixture is stirred for 20 hours and then concentrated to dryness under reduced pressure at 40° C. The residue obtained is taken up in 300 cm³ of water, acidified to pH in the region of 2 by adding 1N aqueous sulphuric acid solution and extracted with 3 times 100 cm³ of ethyl acetate. The combined organic phases are washed with 50 cm³ of water and with 50 cm³ of saturated aqueous sodium chloride solution, dried over magnesium sulphate and concentrated to dryness under reduced pressure at 40° C. 51.6 g of (4R)-3-tert-butoxycarbonyl-2-benzyl-4-thiazolidinecarboxylic acid (isomer A) are thereby obtained in the form of light yellow crystals, melting point 156° C.

F (2RS, 4R) -2-Benzyl-4-thiazolidinecarboxylic acid may be prepared in a manner similar to that described in Example 1E, but starting with 53.7 g of L-cysteine and 56.5 g of phenylacetaldehyde. 75.8 g of (2RS,4R)-2-benzyl-4-thiazolidinecarboxylic acid, melting point 200° C., are thereby obtained.

EXAMPLE 3

The procedure is similar to that described in Example 1, but starting with 2.58 g of benzyl (4R)-3-{3-[2-(4-tert-butoxycarbonyl-2-benzyl-3-thiazolidinyl)-2-oxoethyl]ureido}phenylacetate (isomer A), 1.6 g of ammonium formate and 1.3 g of palladium on charcoal (10% Pd). 1.06 g of (4R) -3-{3-[2-(4-tert-butoxycarbonyl-2-benzyl-3-thiazolidinyl)-2-oxoethyl]ureido}phenylacetic acid (isomer A), melting point 110° C., are thereby obtained; $[\alpha]_D^{25}=-89.0°\pm1.6°$ (C %=0.51; methanol).

NMR (200 MHz, δ in ppm, DMSO-d₆+2 drops of CD₃COOD, 393K) . 1.55 (1s, 9H, —C(CH₃)₃), 2.92 (dd, J=14.0 and 9.5 Hz, 1H, 1H of Ph—CH₂), 3.38 (d, J=7.0 Hz, 2H, S—CH₂—), 3.50 (s, 2H, Ar—CH₂—COO—), 3.53 (dd, J=14.0 and 4.5 Hz, 1H, 1H of Ph—CH₂), 3.95 and 4.05 (2d, J=17.0 Hz, 2H, N—CH₂—CO—), 5.02 (t, J=7.0 Hz, 1H, —N—CH—CO—), 5.50 (dd, J=9.5 and 4.5 Hz, 1H, N—CH—S—) 6.84 (d, J=8.0 Hz, 1H, H at position 4 of Ar—NH—CO), 7.17 (t, J=8.0 Hz, 1H, H at position 5 of Ar—NH—CO—), 7.20 to 7.40 (mt, 7H, Ph of benzyl and 2H of Ar—NH—CO—).

Benzyl (4R)-3-{3-[2-(4-tert-butoxycarbonyl-2-benzyl-3-thiazolidinyl)-2-oxoethyl]ureido}phenylacetate (isomer A) may be prepared in a manner similar to that described in Example 1A, but starting with 2.8 g of tert-butyl (4R) -3-(2-aminoacetyl)-2-benzyl-4-thiazolidinecarboxylate (isomer A) and 2.22 g of benzyl 3-isocyanatophenylacetate. The crude product obtained is purified by chromatography on silica [eluent: ethyl acetate/cyclohexane (40: 60 by volume)]. The fractions containing the expected product are pooled and concentrated to dryness under reduced pressure at 40° C. After vigorous stirring in hexane, 2.82 g of benzyl (4R) -3-{3-[2-(4-tert-butoxycarbonyl-2-benzyl-3-thiazolidinyl)-2-oxoethyl]ureido}phenylacetate (isomer A) are thereby obtained in the form of an amorphous product, which is used in the subsequent syntheses without further treatment.

EXAMPLE 4

0.10 g of potassium hydroxide is added at a temperature in the region of 25° C. to a solution of 0.82 g of methyl (2R,4R)-3-[3-{2-[4-tert-butoxycarbonyl-2-((RS)-1,2,3,6-tetrahydro-1-phenyl)-3-thiazolidinyl]-2-oxoethyl}ureido]phenylacetate in 8 cm³ of a water/methanol (30:70 by volume) mixture. The reaction mixture is stirred for 4 hours at a temperature in the region of 25° C. and then concentrated to approximately one half under reduced pressure. The solution obtained is diluted with 40 cm³ of water, washed with twice 20 cm³ of diethyl ether, then brought to a pH in the region of 2 by adding 1N aqueous sulphuric acid solution and extracted with twice 50 cm³ of ethyl acetate. The combined organic phases are washed successively with 20 cm³ of water and 20 cm³ of saturated aqueous sodium chloride solution, dried over magnesium sulphate and concentrated to dryness under reduced pressure at 40° C. The crude product obtained is purified by chromatography on silica [eluent: methylene chloride/methanol (90:10 by volume)]. The fractions containing the expected product are pooled and concentrated to dryness under reduced pressure at 40° C. 0.31 g of (2R,4R)-3-[3-{2-[4-tert-butoxycarbonyl-2-((RS)-1,2,3,6-tetrahydro-1-phenyl)-3-thiazolidinyl]-2-oxoethyl}ureido]phenylacetic acid is thereby obtained in the form of an amorphous product.

NMR (200 MHz, δ in ppm, DMSO-d₆, 393K}. The mixture of the two diastereoisomers in the proportions 50:50 is observed. 1.10 to 1.50 and from 1.80 to 2.30 (mt, 7H, —CH= and —CH₂— of 1,2,5,6-tetrahydrophenyl), 1.47 and 1.49 (2s, 9H in total, —C(CH₃)₃), 3.25 to 3.45 (mt, 2H, S—CH₂—), 3.45 (t, 2H, Ar—CH₂—COO—), 4.08 (mt, 2H, N—CH₂—CO—), 5.02 (t, J=7.5 Hz, 1H, N—CH—CO—), 5.32 (mt, 1H, N—CH—S—), 5.62 (mt, 2H, —CH=CH— of 1,2,5,6-tetrahydrophenyl), 6.22 (t, J=5.5 Hz, 1H, NH—CO—), 6.84 (d, J=8.0 Hz, 1H, H at position 4 of Ar—NH—CO), 7.13 (t, J=8.0 Hz, 1H, H at position 5 of Ar—NH—CO—), 7.25 to 7.35 (mt, 2H of Ar—NH—CO—), 8.45 (broad s, 1H, 1H of —CO—NH—Ar).

A Methyl (2R, 4R)-3-[3-{2- [4 - tert-butoxycarbonyl-2-((RS)-1,2,3,6-tetrahydro-1-phenyl)-3-thiazolidinyl]-2-oxoethyl}ureido]phenylacetate may be prepared in a manner similar to that described in Example 1A, but starting with 2.18 g of tert-butyl (2R,4R)-3-(2-aminoacetyl)-2-((RS)-1,2,3,6-tetrahydro-1-phenyl)-4-thiazolidinecarboxylate and 1.34 g of methyl 3-isocyanatophenylacetate. The crude product is purified by chromatography on silica [eluent: methylene chloride/ethyl acetate (80:20 by volume)]. The fractions containing the expected product are pooled and concentrated to dryness under reduced pressure at 40° C. 1.15 g of methyl (2R, 4R)-[3-{2-[4-tert-butoxycarbonyl-2-((RS)-1,2,3,6-tetrahydro-1-phenyl)-3-thiazolidinyl]-2-oxoethyl}phenylacetate are thereby obtained in the form of a thick oil, which is used in the subsequent syntheses without further treatment.

B tert-Butyl (2R,4R)-3-(2-aminoacetyl)-2-((RS)-1,2,3,6-tetrahydro-1-phenyl)-4-thiazolidinecarboxylate may be prepared in a manner similar to that described in Example 1B, but starting with 2.28 g of tert-butyl (2R,4R)-3-(2-tert-butoxycarbonylaminoacetyl)-2-((RS)-1,2,3,6-tetrahydro-1-phenyl)-4-thiazolidinecarboxylate and 0.78 cm³ of iodotrimethylsilane. 2.18 g of tert-butyl (2R,4R)-3-(2-aminoacetyl)-2-((RS)-1,2,3,6-tetrahydro-1-phenyl)-4-thiazolidinecarboxylate are thereby obtained in the form of a yellow oil, which is used in the subsequent syntheses without further treatment.

C tert-Butyl (2R,4R)-3-(2-tert-butoxycarbonylaminoacetyl)-2-((RS)-1,2,3,6-tetrahydro-1-phenyl)-4- thiazolidinecarboxylate may be prepared in a manner similar to that described in Example 1C, but starting with 4.4 g of tert-butyl (2RS,4R)-2-((RS)-1,2,3,6-tetrahydro-1-phenyl)-4-thiazolidinecarboxylate, 2.28 g of 2-tert-butoxycarbonylaminoacetic acid and 2.68 g of N,N'-dicyclohexylcarbodiimide. The crude product is purified by chromatography on silica [eluent: ethyl acetate/cyclohexane (75:25 by volume)]. The fractions containing the expected product are pooled and concentrated to dryness under reduced pressure at 40° C. 2.32 g of tert-butyl (2R,4R)-3-(2-tert-butoxycarbonyl-aminoacetyl)-2-((RS)-1,2,3,6-tetrahydro-1-phenyl)-4-thiazolidinecarboxylate are thereby obtained in the form of an oil, which is used in the subsequent syntheses without further treatment.

D tert-Butyl (2RS,4R)-2-((RS)-1,2,3,6-tetrahydro-1-phenyl) thiazolidinecarboxylate may be prepared in a manner similar to that described in Example 2C, but starting with 8.0 g of tert-butyl (2R,4R)-3-tert-butoxycarbonyl-2-((RS)-1,2,3,6-tetrahydro-1-phenyl)-4-thiazolidinecarboxylate and 3.57 cm$^3$ of iodotrimethylsilane. 4.43 g of tert-butyl (2RS,4R)-2-((RS)-1,2,3,6-tetrahydro-1-phenyl)-4-thiazolidinecarboxylate are thereby obtained in the form of a yellow oil, which is used in the subsequent syntheses without further treatment.

E tert-Butyl (2R,4R)-3-tert-butoxycarbonyl-2-((RS)-1,2,3,6-tetrahydro-1-phenyl)-4-thiazolidinecarboxylate may be prepared in a manner similar to that described in Example 2D, but starting with 25.5 g of (2R,4R)-3-tert-butoxycarbonyl-2-((RS)-1,2,3,6-tetrahydro-1-phenyl) thiazolidinecarboxylic acid, 15.5 g of paratoluenesulphonyl chloride and 6.1 g of tert-butanol. 15.2 g of tert-butyl (2R,4R)-3-tert-butoxycarbonyl-2-((RS)-1,2,3,6-tetrahydro-1-phenyl)-4-thiazolidinecarboxylate are thereby obtained in the form of an orange-coloured oil, which is used in the subsequent syntheses without further treatment.

F (2R,4R)-3-tert-Butoxycarbonyl-2-((RS)-1,2,3,6-tetrahydro-1-phenyl)thiazolidinecarboxylic acid may be prepared in a manner similar to that described in Example 2E, but starting with 16.7 g of (2RS,4R)-2-((RS)-1,2,3,6-tetrahydro-1-phenyl)thiazolidinecarboxylic acid, 160 cm$^3$ of 0.5N aqueous sodium hydroxide solution and 17.3 g of di-tert-butyl dicarbonate. 24.6 g of (2R,4R)-3-tert-butoxycarbonyl-2-((RS)-1,2,3,6-tetrahydro-1-phenyl) thiazolidinecarboxylic acid are thereby obtained, which product is used in the subsequent syntheses without further treatment.

G (2RS, 4R) -2- (RS) -1,2,3,6-Tetrahydro-1-phenyl)-4-thiazolidinecarboxylic acid may be prepared in a manner similar to that described in Example 1E, but starting with 12.1 g of L-cysteine and 11.0 g of 1,2,3,6-tetrahydrobenzaldehyde. 18.7 g of (2RS,4R)-2-(RS)-1,2,3,6-tetrahydro-1-phenyl)-4-thiazolidinecarboxylic acid, melting point 236° C., are thereby obtained.

H Methyl 3-isocyanatophenylacetate may be prepared in a manner similar to that described in Example 1F, but starting with i g of charcoal, 6 cm$^3$ of diphosgene and 8.25 g of methyl 3-aminophenylacetate. 9.3 g of methyl 3-isocyanatophenylacetate are thereby obtained in the form of a yellow liquid, which is stored under argon and used in the subsequent syntheses without further treatment.

I Methyl 3-aminophenylacetate may be prepared in the following manner: 3.1 g of palladium on charcoal (5% Pd) and a solution of 60.0 g of methyl 3-nitrophenylacetate in 870 cm$^3$ of methanol are introduced successively into a single-necked flask purged with nitrogen. The suspension is stirred for 4 hours under a hydrogen atmosphere (130 kPa) at a temperature in the region of 25° C. The catalyst is separated by filtration and the filtrate is concentrated to dryness under reduced pressure at 40° C. 51.0 g of methyl 3-aminophenylacetate are thereby obtained in the form of an orange-coloured oil, which is used in the subsequent syntheses without further treatment.

Methyl 3-nitrophenylacetate may be prepared according to the method described by M. Segers and A. Bruylants, Bull. Soc. Chim. Belg., 64, 87 (1955).

EXAMPLE 5

The procedure is as in Example 4, but starting with 0.27 g of methyl (4R)-3-[3-{2-[4-tert-butoxycarbonyl-2-[(2RS)-5-norbornen-2-yl]-3-thiazolidinyl]-2-oxoethyl}ureido] phenylacetate (mixture of isomers A and B) and 0.033 g of potassium hydroxide. 0.09 g of (4R) -3- [3-{2- [4-tert-butoxycarbonyl-2-[(2RS)-5-norbornen-2-yl]-3-thiazolidinyl]-2-oxoethyl}ureido]-phenylacetic acid (mixture of isomers A and B) is thereby obtained in the form of an amorphous white product.

NMR (200 MHz, δ in ppm, DMSO-d$_6$+2 drops of CD$_3$COOD, 393K). 0.60 to 2.90 (mt, 7H, —CH— and —CH$_2$— of norbornenyl), 1.50 (s, 9H, C(CH$_3$)$_3$), 3.25 to 3.55 (mt, 2H, S—CH$_2$—), 3.50 (s, 2H, Ar—CH$_2$—COO—), 3.95 and 4.13 (2d, J=17.0 Hz, 2H, N—CH$_2$—CO—), 4.96 (d, J=11.0 Hz, 1H, —N—CH—S—), 5.02 (dd, J=8.0 and 6.0 Hz, 1H, —N—CH—CO—), 6.23 (mt, 2H, —CH=CH— of norbornenyl), 6.83 (d, J=8.0 Hz, 1H, H at position 4 of Ar—NH—CO—), 7.15 (t, J=8.0 Hz, 1H, H at position 5 of Ar—NH—CO—), 7.20 to 7.40 (mt, 2H of Ar—NH—CO—).

EXAMPLE 6

The procedure is as in Example 1A, but starting with 0.9 g of tert-butyl (4R)-3-(2-aminoacetyl)-2-[(2RS)-5-norbornen-2-yl]-4-thiazolidinecarboxylate (mixture of isomers A and B) and 0.57 g of methyl 3-isocyanatophenylacetate. The crude product is purified by chromatography on silica [eluent: ethyl acetate/cyclohexane (40:60 by volume)]. The fractions containing the expected product are pooled and concentrated to dryness under reduced pressure at 40° C. 0.4 g of methyl (4R)-3-[3-{2-[4-tert-butoxycarbonyl-2-[(2RS)-5-norbornen-2-yl]-3-thiazolidinyl]-2-oxoethyl}-ureido]phenylacetate (mixture of isomers A and B) is thereby obtained in the form of an amorphous product.

NMR (200 MHz, δ in ppm, DMSO-d$_6$, 393K). 0.50 to 2.90 (mt, 7H, —CH— and —CH$_2$— of norbornenyl), 1.50 (s, 9H, C(CH$_3$)3) 3.20 to 3.60 (mt, 2H, S—CH$_2$—), 3.60 (s, 5H, Ar—CH$_2$—COOCH$_3$), 3.90 and 4.10 (2dd, J=17.0 and 5.5 Hz, 2H, N—CH$_2$—CO—), 4.92 (d, J=11.5 Hz, 1H, —N—CH—S—), 5.12 (dd, J=8.0 and 6.0 Hz, 1H, —N—CH—CO—) 6.20 (mt, 2H, —CH=CH— of norbornenyl), 6.42 (t, J=5.5 Hz, 1H, NH—CO—), 6.80 (d, J=8.0 Hz, 1H, H at position 4 of Ar—NH—CO), 7.17 (t, J=8.0 Hz, 1H, H at position 5 of Ar—NH—CO—), 7.20 to 7.40 (mt, 2H of Ar—NH—CO—), 8.86 (broad s, 1H, —CO—NH—Ar).

tert-Butyl (4R) -3-2-aminoacetyl) -2- [(2RS) -5-norbornen-2-yl]-4-thiazolidinecarboxylate (mixture of isomers A and B) may be prepared in a manner similar to that described in Example 1B, but starting with 0.95 g of tert-butyl (4R) -3- (2-tert-butoxycarbonylaminoacetyl)-2-[(2RS)-5-norbornen-2-yl]-4-thiazolidinecarboxylate (mixture of isomers A and B) and 0.32 cm$^3$ of iodotrimethylsilane. 0.7 g of tert-butyl (4R) -3- (2-aminoacetyl) -2-[(2RS) -5-norbornen-2-yl]-4-thiazolidinecarboxylate (mixture of isomers A and B) is thereby obtained in the form of an orange-coloured oil, which is used in the subsequent syntheses without further treatment.

tert-Butyl (4R)-3-(2-tert-butoxycarbonylaminoacetyl)-2-[(2RS)-5-norbornen-2-yl]-4-thiazolidinecarboxylate (mixture of isomers A and B) may be prepared in a manner similar to that described in Example 1C, but starting with 2.3 g of tert-butyl (4R)-2-[(2RS)-5-norbornen-2-yl]-4-thiazolidinecarboxylate (mixture of isomers A and B), 1.4 g of 2-tert-butoxycarbonylaminoacetic acid and 1.68 g of N,N'-dicyclohexylcarbodiimide. The crude product is purified by chromatography on silica [eluent: ethyl acetate/cyclohexane (30:70 by volume)]. The fractions containing the expected product are pooled and concentrated to dryness under reduced pressure at 40° C. 1.5 g of tert-butyl (4R) -3- (2-tert-butoxycarbonylaminoacetyl)-2-[(2RS)-5-norbornen-2-yl]-4-thiazolidinecarboxylate (mixture of isomers A and B) are thereby obtained in the form of a yellow oil, which is used in the subsequent syntheses without further treatment.

tert-Butyl (4R)-2-[(2RS)-5-norbornen-2-yl]-4-thiazolidinecarboxylate (mixture of isomers A and B) may be prepared in a manner similar to that described in Example 2C, but starting with 3.0 g of tert-butyl (4R)-3-tert-butoxycarbonyl-2-[(2RS)-5-norbornen-2-yl]-4-thiazolidinecarboxylate (mixture of isomers A and B) and 1.24 cm$^3$ of iodotrimethylsilane. 2.3 g of tert-butyl (4R)-2-[(2RS)-5-norbornen-2-yl]-4-thiazolidinecarboxylate (mixture of isomers A and B) are thereby obtained in the form of a yellow oil, which is used in the subsequent syntheses without further treatment.

tert-Butyl (4R)-3-tert-butoxycarbonyl-2-[(2RS)-5-norbornen-2-yl]-4-thiazolidinecarboxylate (mixture of isomers A and B) may be prepared in a manner similar to that described in Example 2D, but starting with 46.0 g of (4R)-3-tert-butoxycarbonyl-2-[(2RS)-5-norbornen-2-yl]-4-thiazolidinecarboxylic acid (mixture of isomers), 26.6 g of para-toluenesulphonyl chloride and 10.5 g of tert-butanol. The crude product is purified by chromatography on silica [eluent: ethyl acetate/cyclohexane (30:70 by volume)]. The fractions containing the expected product are pooled and concentrated to dryness under reduced pressure at 40° C. 40.0 g of tert-butyl (4R)-3-tert-butoxycarbonyl-2-[(2RS}-5-norbornen-2-yl]-4-thiazolidinecarboxylate (mixture of isomers A, B, C and D) are thereby obtained in the form of an orange-coloured oil. A second chromatographic run on silica [eluent: ethyl acetate/cyclohexane (5:95 by volume)] carried out on 6.0 g of this mixture enables 0.3 g of tert-butyl (4R) - 3 -tert -butoxycarbonyl -2-[(2RS)-5-norbornen-2-yl]-4-thiazolidinecarboxylate (mixture of isomers A and B) (first elution products) and 3.5 g of tert-butyl (4R)-3-tert-butoxycarbonyl-2-[(2RS)-5-norbornen-2-yl]-4-thiazolidinecarboxylate (mixture of isomers C and D) to be isolated in the form of yellow oils, which are used in the subsequent syntheses without further treatment.

(4R)-3-tert-Butoxycarbonyl-2-[(2RS)-5-norbornen-2-yl]-4-thiazolidinecarboxylic acid (mixture of isomers) may be prepared in a manner similar to that described in Example 2E, but starting with 40.0 g of (4R) -2- [(2RS) -5-norbornen-2-yl]-4-thiazolidinecarboxylic acid (mixture of isomers), 360 cm$^3$ of 0.5N aqueous sodium hydroxide solution and 39.0 g of di-tert-butyl dicarbonate. 46.0 g of (4R)-3-tert-butoxycarbonyl-2-[(2RS)-5-norbornen-2-yl]-4-thiazolidinecarboxylic acid (mixture of isomers) are thereby obtained, which product is used in the subsequent syntheses without further treatment.

(4R) -2- [(2RS) -5-Norbornen-2-yl]-4-thiazolidinecarboxylic acid (mixture of isomers) may be prepared in a manner similar to that described in Example 1E, but starting with 23.0 g of L-cysteine and 25.0 g of (RS)-2-(5-norbornenyl) carboxaldehyde (mixtures of endo and exo isomers). 40.0 g of (4R)-2-[(2RS)-5-Norbornen-2-yl]-4-thiazolidinecarboxylic acid (mixture of isomers), melting point 220° C., are thereby obtained, which product is used in the subsequent syntheses without further treatment.

EXAMPLE 7

The procedure is as in Example 4, but starting with 0.6 g of methyl (4R)-3-[3-{2-[4-tert-butoxycarbonyl-2-[(2RS)-5-norbornen-2-yl]-3-thiazolidinyl]-2-oxoethyl}ureido] phenylacetate (mixture of isomers C and D) and 0.074 g of potassium hydroxide. 0.03 g of (4R) -3- [3-{2-[4-tert-butoxycarbonyl-2-[(2RS) -5-norbornen-2-yl]-3-thiazolidinyl]-2-oxoethyl}ureido]-phenylacetic acid (mixture of isomers C and D) is thereby obtained in the form of an amorphous white product.

NMR (200 MHz, δ in ppm, DMSO-d$_6$+2 drops of 2 drops of CD$_3$COOD, 393K). From 1.00 to 1.90 and from 2.20 to 2.9 (mt, 7H, —CH— and —CH$_2$— of norbornenyl), 1.50 (s, 9H, C(CH$_3$)$_3$), 3.42 (AB, 2H, S—CH$_2$—), 3.48 (s, 2H, Ar—CH$_2$—COO), 4.02 (mt, 2H, N—CH$_2$—CO—), 4.97 (t, J=7.5 Hz, 1H, —N—OH—CO—), 5.30 (mt, 1H, —N—CH—S—), from 6.00 to 6.40 (mt, 2H, —CH=CH— of norbornenyl), 6.81 (d, J=8.0 Hz, 1H, H at position 4 of Ar—NH—CO), 7.12 (t, J=8.0 Hz, 1H, H at position 5 of Ar—NH—CO—), 7.20 to 7.40 (mt, 2H of Ar—NH—CO—).

Methyl (4R)-3-[3-{2-[4-tert-butoxycarbonyl-2-[(2RS)-5-norbornen-2-yl]-3-thiazolidinyl]-2-oxoethyl}ureido] phenylacetate (mixture of isomers C and D) may be prepared in a manner similar to that described in Example 1A, but starting with 0.77 g of tert-butyl (4R)-3-(2-aminoacetyl) -2-[(2RS)-5-norbornen-2-yl]-4-thiazolidinecarboxylate (mixture of isomers C and D) and 0.57 g of methyl 3-isocyanatophenylacetate. The crude product is purified by chromatography on silica [eluent: ethyl acetate/cyclohexane (40:60 by volume)]. The fractions containing the expected product are pooled and concentrated to dryness under reduced pressure at 40° C. 0.6 g of methyl (4R)-3-[3-{2-[4-tert-butoxycarbonyl-2-[(2RS)-5-norbornen-2-yl]-3-thiazolidinyl]-2-oxoethyl}ureido]phenylacetate (mixture of isomers C and D) is thereby obtained in the form of a yellow oil, which is used in the subsequent syntheses without further treatment.

tert-Butyl (4R)-3-2-aminoacetyl)-2-[(2RS)-5-norbornen-2-yl]-4-thiazolidinecarboxylate (mixture of isomers C and D) may be prepared in a manner similar to that described in Example 1B, but starting with 1.0 g of tert-butyl (4R)-3-(2-tert-butoxycarbonylaminoacetyl)-2-[(2RS)-5-norbornen-2-yl]-4-thiazolidinecarboxylate (mixture of isomers C and D) and 0.36 cm$^3$ of iodotrimethylsilane. 0.77 g of tert-butyl (4R)-3-(2-aminoacetyl)-2-[(2RS)-5-norbornen-2-yl]-4-thiazolidinecarboxylate (mixture of isomers C and D) is thereby obtained in the form of a yellow oil, which is used in the subsequent syntheses without further treatment.

tert-Butyl (4R) -3-(2-tert-butoxycarbonylaminoacetyl)-2-[(2RS)-5-norbornen-2-yl]-4-thiazolidinecarboxylate (mixture of isomers C and D) may be prepared in a manner similar to that described in Example 1C, but starting with 2.8 g of tert-butyl (4R) -2-[(2RS)-5-norbornen-2-yl]-4-thiazolidinecarboxylate (mixture of isomers C and D), 1.75 g of 2-tert-butoxycarbonylaminoacetic acid and 2.0 g of N,N'-dicyclohexylcarbodiimide. The crude product is purified by chromatography on silica [eluent: ethyl acetate/ cyclohexane (35:65 by volume)]. The fractions containing the expected product are pooled and concentrated to dryness under reduced pressure at 40° C. 2.0 g of tert-butyl (4R) -3-(2-tert-butoxycarbonylaminoacetyl)-2-[(2RS)-5-norbornen-2-yl]-4-thiazolidinecarboxylate (mixture of isomers C and D) are thereby obtained in the form of a yellow oil, which is used in the subsequent syntheses without further treatment.

tert-Butyl (4R) -2-[(2RS)-5-norbornen-2-yl)-4-thiazolidinecarboxylate (mixture of isomers C and D) may be prepared in a manner similar to that described in Example 2C, but starting with 4.3 g of tert-butyl (4R) - 3 -tert -butoxycarbonyl-2-[(2RS)-5-norbornen -2-yl]-4-thiazolidinecarboxylate (mixture of isomers C and D) and 4.2 cm$^3$ of iodotrimethylsilane. 2.8 g of tert-butyl (4R) -2-[(2RS)-5-norbornen-2-yl]-4-thiazolidinecarboxylate (mixture of isomers C and D) are thereby obtained in the form of a colourless oil, which is used in the subsequent syntheses without further treatment.

EXAMPLE 8

The procedure is as in Example 1, but starting with 0.2 g of benzyl (4R)-3-[3-{2-[4-tert-butoxycarbonyl-2-[(2RS)-5-norbornen-2-yl]-3-thiazolidinyl]-2-oxoethyl}ureido]phenylacetate (mixture of isomers C and D), 0.13 g of Ammonium formate and 0.2 g of palladium on charcoal (10% Pd). 0.07 g of (4R)-3-[3-{2-[4-tert-butoxycarbonyl-2-((2RS) -2-norbornyl)-3-thiazolidinyl]-2-oxoethyl}ureido] phenylacetic acid (mixture of isomers C and D) is thereby obtained in the form of a white product, melting point 115° C.

NMR (200 MHz, δ in ppm, DMSO-d$_6$+2 drops of CD$_3$COOD). A mixture of rotamers and isomers is observed. From 1.00 to 2.50 (mt, 11H, —CH— and —CH$_2$— of norbornyl), 1.35 to 1.50 (mt, 9H, C(CH$_3$)$_3$), 3.10 to 3.50 (mt, 2H, S—CH$_2$—), 3.50 (s, 2H, Ar—CH$_2$—COO), 3.80 to 4.30 (mt, 2H, N—CH$_2$—CO—), from 4.70 to 5.20 (mt, 1H, —N—CH—CO—), 5.10 to 5.70 (mt, 1H, —N—CH—S—), from 6.80 to 6.95 (mt, 1H, H at position 4 of Ar—NH—CO), 7.18 (t, J=8.0 Hz, 1H, H at position 5 of Ar—NH—CO—), 7.30 to 7.45 (mt, 2H of Ar—NH—CO—).

Benzyl (4R) -3- [3-{2- [4-tert-butoxycarbonyl-2-[(2RS)-5-norbornen-2-yl]-3-thiazolidinyl]-2-oxoethyl}ureido] phenylacetate (mixture of isomers C and D) may be prepared in a manner similar to that described in Example 1A, but starting with 1.6 g of tert-butyl (4R) -3- (2 -aminoacetyl) -2- [(2RS) -5-norbornen-2-yl]-4-thiazolidinecarboxylate (mixture of isomers C and D) and 1.26 g of benzyl 3-isocyanatophenylacetate. The crude product is purified by chromatography on silica [eluent: ethyl acetate/diisopropyl ether (10:90 by volume)]. The fractions containing the expected product are pooled and concentrated to dryness under reduced pressure at 40° C. 0.2 g of benzyl (4R)-3-[3-{2-[4-tert-butoxycarbonyl-2-[(2RS)-5-norbornen-2-yl]-3-thiazolidinyl]-2-oxoethyl}ureido]phenylacetate (mixture of isomers C and D) is thereby obtained in the form of an amorphous product, which is used in the subsequent syntheses without further treatment.

EXAMPLE 9

The procedure is as in Example 1A, but starting with 0.35 g of tert-butyl (4R)-3-(2-aminoacetyl)-2-[(2RS)-5-norbornen-2-yl]-4-thiazolidinecarboxylate (mixture of isomers) and 0.14 g of 3-methylphenyl isocyanate. The crude product is purified by chromatography on silica [eluent: methylene chloride/methanol (99.1 by volume)]. The fractions containing the expected product are pooled and concentrated to dryness under reduced pressure at 40° C. After recrystallazation in diisopropyl ether, 0.1 g of tert-butyl (4R) -3-{2-[3-(3-methylphenyl) ureido]acetyl}-2-[ (RS)-5-norbornen-2-yl]thiazolidinecarboxylate (mixture of isomers) is thereby obtained in the form of a white solid, melting point 114° C.

NMR (200 MHz, δ in ppm, DMSO-d$_6$+2 drops of CD$_3$COOD). 0.40 to 1.90 and from 2.20 to 2.90 (mt, 7H, —CH— and —CH$_2$— of norbornenyl), 1.58 (s, 9H, C(CH$_3$)$_3$), 2.27 (s, 3H, Ar—CH$_3$), 3.44 (AB, 2H, S—CH$_2$—), 3.92 and 4.12 (2d, J=17.0 Hz, 2H, N—CH$_2$—CO—), 4.93 (d, J=11.5 Hz, 1H, —N—CH—S—), 5.12 (mt, 1H, —N—CH—CO—), 6.22 (mt, 2H, —CH—CH— of norbornenyl), 6.74 (d, J=8.0 Hz, 1H, H at position 4 of Ar—NH—CO), 7.12 (t, J=8.0 Hz, 1H, H at position 5 of Ar—NH—CO—), 7.15 to 7.35 (mt, 2H of Ar—NH—CO—).

tert-Butyl (4R)-3(2-aminoacetyl)-2-[(2RS)-5-norbornen-2-yl]-4-thiazolidinecarboxylate (mixture of isomers) may be prepared as in Example 1B, but starting with 0.70 g of tert-butyl (4R)-3-(2-tert-butoxy-carbonylaminoacetyl)-2-[(2RS)-5-norbornen-2-yl]-4-thiazolidinecarboxylate (mixture of isomers) and 0.23 cm$^3$ of iodotrimethylsilane. 0.35 g of tert-butyl (4R)-3-(2-aminoacetyl)-2-[(2RS)-5-norbornen-2-yl]-4-thiazolidinecarboxylate (mixture of isomers) is thereby obtained in the form of an orange-coloured oil, which is used in the subsequent syntheses without further treatment.

tert-Butyl (4R)-3-(2-tert-butoxycarbonylaminoacetyl)-2-[(2RS)-5-norbornen-2-yl)-4-thiazolidinecarboxylate (mixture of isomers) may be prepared in a manner similar to that described in Example 1C, but starting with 4.75 g of tert-butyl (4R)-2-[(2RS)-5-norbornen-2-yl]-4-thiazolidinecarboxylate (mixture of isomers), 2.96 g of 2-tert-butoxycarbonylaminoacetic acid and 3.48 g of N,N'-dicyclohexylcarbodiimide- The crude product is purified by chromatography on silica [eluent: ethyl acetate/cyclohexane (30:70 by volume)]. The fractions containing the expected product are pooled and concentrated to dryness under reduced pressure at 40° C. 1.36 g of tert-butyl (4R)-3-(2-tert-butoxycarbonylaminoacetyl)-2-[(2RS)-5-norbornen-2-yl]-4-thiazolidinecarboxylate (mixture of isomers) are thereby obtained in the form of an orange-yellow amorphous product, which is used in the subsequent syntheses without further treatment.

tert-Butyl (4R)-2-[(2RS)-5-norbornen-2-yl]-4-thiazolidinecarboxylate (mixture of isomers) may be prepared in a manner similar to that described in Example 2C, but starting with 6.3 g of tert-butyl (4R)-3-tert-butoxycarbonyl-2-[(2RS)-5-norbornen-2-yl]-4-thiazolidinecarboxylate (mixture of isomers) and 2.41 cm$^3$ of iodotrimethylsilane. 4.75 g of tert-butyl (4R)-2-[(2RS)-5-norbornen-2-yl]-4-thiazolidinecarboxylate (mixture of isomers) are thereby obtained in the form of a yellow oil, which is used in the subsequent syntheses without further treatment.

EXAMPLE 10

The procedure is as in Example 1, but starting with 0.57 g of benzyl (4R) -3-{3- [2- (4-tert-butoxycarbonyl-2-tert-butyl-3-thiazolidinyl)-2-oxoethyl]ureido)phenylacetate (isomer A), 0.50 g of ammonium formate and 0.5 g of palladium on charcoal (10% Pd). 0.07 g of (4R)-3-{3-2-(4-tert-butoxycarbonyl-2-tert-butyl-3-thiazolidinyl)-2-oxoethyl]ureido}phenylacetic acid (isomer A) is thereby obtained in the form of an amorphous product.

NMR (200 MHz, δ in ppm, DMSO-d$_6$. 0.92 (s, 9H, C(CH$_3$)$_3$), 1.48 (s, 9H, COOC(CH$_3$)$_3$), from 3.20 to 3.65 (mt, 2H, S—CH$_2$—), 3.34 (s, 2H, Ar—CH$_2$COO), 3.90 and 4.10 (2dd, J=17.0 and 5.5 Hz, 2H, N—CH$_2$—CO—), 5.14 (t, J=7.5 Hz, 1H, —N—CH—CO—), 5.40 (s, 1H, —N—CH—S—), 6.50 (t, J=5.5 Hz, 1H, —N—CH—CO—), 6.80 (d, J=8.0 Hz, 1H, H at position 4 of Ar—NH—CO), 7.15 (t, J=8.0 Hz, 1H, H at position 5 of Ar—NH—CO—), 7.20 to 7.30 (mt, 2H of Ar—NH—CO—), 8.90 (s, 1H, —CO—NH—Ar).

Benzyl (4R)-3-{3-[2-(4- tert-butoxycarbonyl-2-tert-butyl-3-thiazolidinyl)-2-oxoethyl]-ureido}phenylacetate (isomer A) may be prepared in a manner similar to that described in Example 1A, but starting with 0.9 g of tert-butyl (4R)-3-(2-aminoacetyl)-2-tert-butyl-4-thiazolidinecarboxylate (isomer A) and 1.18 g of benzyl 3-isocyanatophenylacetate. The crude product is purified by chromatography on silica [eluent: ethyl acetate/methylene chloride (10:90 by volume)]. The fractions containing the expected product are pooled and concentrated to dryness under reduced pressure at 40° C. 0.81 g of benzyl (4R)-3-{3-[2-(4-tert-butoxycarbonyl-2-tert-butyl-3-thiazolidinyl)-2-oxoethyl]ureido}phenylacetate (isomer A) is thereby obtained in the form of a thick oil, which is used in the subsequent syntheses without further treatment.

tert-Butyl (4R) -3- (2-aminoacetyl) -2-tert-butyl-4-thiazolidinecarboxylate (isomer A) may be prepared as in Example 1B, but starting with 2.0 g of tert-butyl (4R)-3-(2-tert-butoxycarbonylaminoacetyl)-2-tert-butyl-4-thiazolidinecarboxylate (isomer A) and 0.75 cm$^3$ of iodotrimethylsilane. 0.9 g of tert-butyl (4R)-3-(2-aminoacetyl)-2-tert-butyl-4-thiazolidinecarboxylate (isomer A) is thereby obtained in the form of a yellow oil, which is used in the subsequent syntheses without further treatment.

tert-Butyl (4R)-3-(2-tert-butoxycarbonyl-aminoacetyl)-2-tert-butyl-4-thiazolidinecarboxylate (isomer A) may be prepared in a manner similar to that described in Example 1C, but starting with 8.0 g of tert-butyl (2RS,4R)-2-tert-butyl-4-thiazolidinecarboxylate, 5.71 g of 2-tert-butoxycarbonyl-aminoacetic acid and 6.7 g of N,N'-dicyclohexylcarbodiimide. The crude product is purified by chromatography on silica [eluent: ethyl acetate/cyclohexane (20:80 by volume)]. The fractions containing the expected product are pooled and concentrated to dryness under reduced pressure at 40° C. 2.0 g of tert-butyl (4R)-3-(2-tert-butoxycarbonyl-aminoacetyl-2-tert-butyl-4-thiazolidinecarboxylate (isomer A) are thereby obtained in the form of a colourless oil, which is used in the subsequent syntheses without further treatment.

tert-Butyl (2RS,4R)-2-tert-butyl-4-thiazolidinecarboxylate may be prepared in a manner similar to that described in Example 1D, but starting with 10.0 g of (2RS,4R)-2-tert-butyl-4-thiazolidinecarboxylic acid dissolved in 200 cm$^3$ of chloroform, 5 cm$^3$ of concentrated sulphuric acid and an excess of isobutene. 13.0 g of tert-butyl (2RS,4R)-2-tert-butyl-4-thiazolidinecarboxylate are thereby obtained in the form of a yellow oil, which is used in the subsequent syntheses without further treatment.

(2RS,4R)-2-tert-Butyl-4-thiazolidinecarboxylic acid may be prepared in a manner similar to that described in Example in Example 1E, but starting with 7.6 g of L-cysteine and 5.17 g of pivalaldehyde. 10.4 g of (2RS,4R)-2-tert-butyl-4-thiazolidinecarboxylic acid, melting point 184° C., are thereby obtained.

EXAMPLE 11

The procedure is similar to that described in Example 1, but starting with 1.36 g of tert-butyl-(4R)-3-[2-{3-[(S) -3-(1-benzyloxycarbonylethyl) phenyl]-ureido}acetyl]-2-butylthiazolidinecarboxylate (isomer A), 0.9 g of ammonium formate and 1.3 g of palladium on charcoal (10% Pd). 0.65 g of (S) -3-{3- [2- ((4R) -4-tert-butoxycarbonyl-2-butyl-3-thiazolidinyl)-2-oxoethyl]ureido}-2-phenylpropionic acid (isomer A), melting point 102° C., is thereby obtained; $[\alpha]_D^{25}=-1.1°\pm0.8°$ (C % =0.53; DMF).

NMR (200 MHz, δ in ppm, DMSO-d$_6$+2 drops of CD$_3$COOD). 0.90 (t, 3H: —CH$_2$—C—CH$_3$), 1.40 (mt, 7H: —CH$_2$—CH$_2$—CH$_3$ and —CH$_3$), 1.50 [s, 9H: —COOC(CH$_3$)$_3$], from 1.50 to 2.15 (mt, 2H: —CH$_2$—), from 3.20 to 3.50 (mt, 2H: —S—CH$_2$—), 3.67 (q, 1H: Ar—CH—COO—), from 3.95 to 4.10 (mt, 2H: N—CH$_2$—CO—), 4.97 (t, 1H: N—CH—CO—), 5.35 (dd, 1H: N—CH—S—), 6.25 (residual unres.comp.: —NH—CO—), 6.90 [broad d, 1H: Ar(-H 5)], 7.19 [t, 1H: Ar (-H 5)], from 7.25 to 7.40 [mt, 2H: Ar (-){2 and -}{6)], (residual unres.comp.: Ar—NH—CO—).

A tert-Butyl (4R)-3-[2-{3-[(S)-3-(1-benzyloxycarbonylethyl)phenyl]ureido}acetyl]-2-butylthiazolidinecarboxylate (isomer A) may be prepared in a manner similar to that described in Example 1A, but starting with 2.4 g of tert-butyl-(4R)-3-(2-aminoacetyl)-2-butyl-4-thiazolidinecarboxylate (isomer A) and 2.3 g of benzyl (S)-2-(3-isocyanatophenyl)-propionate.

The crude product obtained is purified by chromatography on silica [eluent: diisopropyl ether/ethyl acetate (95:5 by volume)]. The fractions containing the expected product are pooled and concentrated to dryness under reduced pressure at 40° C. 2.0 g of tert-butyl-(4R)-3-[2-{3-[(S)-3-(1-benzyloxycarbonylethyl)phenyl]ureido}acetyl]-2-butylthiazolidinecarboxylate (isomer A) are thereby obtained in the form of an amorphous product, which is used in the subsequent syntheses without further treatment.

B tert-Butyl (4R) -3- (2-aminoacetyl) -2-butyl-4-thiazolidinecarboxylate (isomer A) may be prepared in a manner similar to that described in Example 1B, but starting with 10.0 g of tert-butyl (4R)-3-(2-tert-butoxycarbonylaminoacetyl)-2-butyl-4-thiazolidinecarboxylate (isomer A) and 4.0 cm$^3$ of iodotrimethylsilane. 5.9 g of tert-butyl (4R)-3-(2-aminoacetyl)-2-butyl-4-thiazolidinecarboxylate (isomer A) are thereby obtained in the form of a yellow oil, which is used in the subsequent syntheses without further treatment.

C tert-Butyl (4R)-3-(2-tert-butoxycarbonylaminoacetyl)-2-butyl-4-thiazolidinecarboxylate (isomer A) may be prepared in a manner similar to that described in Example 1C, but starting with 25.0 g of tert-butyl (2RS,4R)-2-butyl-4-thiazolidinecarboxylate, 12.3 g of 2-tert-butoxycarbonylaminoacetic acid and 14.4 g of N,N'-dicyclohexylcarbodiimide. The crude product is purified by chromatography on silica [eluent: methylene chloride/methanol (99:1 by volume)]. The fractions containing the expected product are pooled and concentrated to dryness under reduced pressure at 40° C. 12.5 g of tert-butyl (4R)-3-(1-tert-butoxycarbonylaminoacetyl)-2-butyl-4-thiazolidine-carboxylate (isomer A) are thereby obtained in the form of a cream-coloured foam, which is used in the subsequent syntheses without further treatment.

D tert-Butyl-(2RS,4R)-2-butyl-4-thiazolidinecarboxylate may he prepared in a manner similar to that described in Example 1D, but starting with 50.0 g of (2RS,4R)-2-butyl-4-thiazolidinecarboxylic acid suspended in 650 cm$^3$ of chloroform, 13 cm$^3$ of concentrated sulphuric acid and an excess of isobutene. 25.0 g of tert-butyl (2RS,4R)-2-butyl-4-thiazolidinecarboxylate are thereby obtained in the form of a yellow oil, which is used in the subsequent syntheses without further treatment.

E (2RS,4R)-2-Butyl-4-thiazolidinecarboxylic acid may be prepared in a manner similar to that described in Example 1E, but starting with 39.0 g of L-cysteine and 30.1 g of valeraldehyde. 52.4 g of (2RS,4R)-2-butyl-4-thiazolidinecarboxylic acid, melting point 195° C., are thereby obtained, which product is used in the subsequent syntheses without further treatment. [Benzyl (S)-2-(3-isocyanatophenyl)propionate may be prepared as in Example 1F, but starting with 2.85 g of benzyl (S)-2-(3-aminophenyl)propionate, 1.48 cm³ of trichloromethyl chloroformate and 0.24 g of charcoal. 3.1 g of benzyl (S)-2-(3-isocyanatophenyl)propionate are thereby obtained in the form of an oil, which is used in the subsequent syntheses without further treatment.

G Benzyl (S)-2-(3-aminophenyl)propionate may be prepared in the following manner: 75 g of ammonium chloride and 37.0 g of powdered zinc are added to a solution of 8.0 g of benzyl (S)-2-(3-nitrophenyl)propionate in a mixture of 35 cm³ of methanol and 300 cm³ of water. The reaction medium is heated to reflux for one hour, then cooled to a temperature in the region of 0° C. and filtered. The filtrate is extracted with three times 200 cm³ of diethyl ether. The organic phases are combined, washed successively with 100 cm³ of water and then 100 cm³ of saturated aqueous sodium chloride solution, dried over magnesium sulphate and concentrated under reduced pressure. 6.7 g of benzyl (S)-2-(3-aminophenyl)propionate are thereby obtained in the form of a yellow oil, which is used in the subsequent syntheses without further treatment.

H Benzyl (S)-2-(3-nitrophenyl)propionate may be prepared in the following manner: 4.72 cm³ of oxalyl chloride are added to a mixture containing 9.75 g of (S)-2-(3-nitrophenyl)propionic acid and 0.5 cm³ of N,N-dimethylformamide in 100 cm³ of 1,2-dichloroethane. The reaction medium is stirred for three hours at a temperature in the region of 25° C., and 5.4 g of benzyl alcohol are then added. Stirring is continued for 12 hours at this same temperature, and the reaction mixture is then washed successively with twice 200 cm³ of saturated aqueous sodium hydrogen carbonate solution, 100 cm³ of water and 100 cm³ of saturated aqueous sodium chloride solution. The organic phases are combined, washed successively with 100 cm³ of water and then 100 cm³ of saturated aqueous sodium chloride solution, dried over magnesium sulphate and concentrated under reduced pressure. The residue is purified by chromatography on silica [eluent: ethyl acetate/cyclohexane (30:70 by volume)]. The fractions containing the expected product are pooled and concentrated under reduced pressure. 11.5 g of benzyl (S)-2-(3-nitrophenyl)propionate are thereby obtained in the form of a yellow oil, which is used in the subsequent syntheses without further treatment.

I (S)-2-(3-Nitrophenyl)propionic acid may be prepared in the following manner: a solution of 21.5 g of (S)-2-(3-nitrophenyl)-N-[(R)-2-hydroxy-1-phenylethyl] propionamide in a mixture of 450 cm³ of 1,4-dioxane and 450 cm³ of 4N aqueous hydrochloric acid solution is heated to a temperature in the region of 80° C. for 5 hours and then stirred for 12 hours at a temperature in the region of 20° C. The reaction medium is concentrated to one half by evaporation under reduced pressure, diluted by adding 500 cm³ of distilled water and extracted with twice 500 cm³ of diethyl ether. The organic phases are combined, washed successively with three times 250 cm³ of water and then 250 cm³ of saturated aqueous sodium chloride solution, dried over magnesium sulphate and concentrated under reduced pressure. 14 g of (S)-2-(3-nitrophenyl)propionic acid are thereby obtained in the form of a cream-coloured solid, which is used in subsequent syntheses without further treatment.

J (S)-2-(3-Nitrophenyl)-N-[(R)-2-hydroxy-1-phenylethyl] propionamide may be prepared in the following manner: 17.2 cm³ of oxalyl chloride are added slowly to a mixture containing 39.0 g of (RS)-2-(3-nitrophenyl)propionic acid and 0.5 cm³ of N,N-dimethylformamide in 400 cm³ of 1,2-dichloroethane. The reaction medium is stirred for 3 hours at a temperature in the region of 20° C. and then concentrated under reduced pressure. The residue is dissolved in 150 cm³ of 1,2-dichloroethane and added to a solution of 27.4 g of (R)-2-phenylglycinol while the temperature of the reaction medium is maintained below 10° C. The reaction mixture is stirred for 12 hours at a temperature in the region of 20° C., and is then washed successively with 1000 cm³ of distilled water, 500 cm³ of normal aqueous hydrochloric acid solution, twice 500 cm³ of distilled water and 500 cm³ of saturated aqueous sodium chloride solution. The organic phase is dried over magnesium sulphate and concentrated under reduced pressure. The two diastereoisomers obtained are separated by chromatography on silica [eluent: methylene chloride/ethyl acetate (70:30 by volume)]. The fractions containing each of the two diastereoisomers are pooled and concentrated under reduced pressure. 21.0 g of (R)-2-(3-nitrophenyl)-N-[(R)-2-hydroxy-1-phenylethyl] propionamide (first elution product), melting point 135° C., and 19.0 g of (S)-2-(3-nitrophenyl)-N-[(R) -2-hydroxy-1-phenylethyl]propionamide (second elution product), melting point 150° C., are thereby obtained.

(RS) -2 - (3 -Nitrophenyl) propionic acid may be prepared according to the method described by E. FELDER et al., J. Med. Chem., 13, 559 (1970).

EXAMPLE 12

The procedure is similar to that described in Example 1A, but starting with 1.2 g of tert-butyl (4R)-3-(2-aminoacetyl) -2-butyl-4-thiazolidinecarboxylate (isomer A) and 0.53 g of 3-methylphenyl isocyanate. The crude product is purified by chromatography on silica [eluent: diisopropyl ether/ethyl acetate (95:5 by volume)]. The fractions containing the expected product are pooled and concentrated to dryness under reduced pressure at 40° C. 0.8 g of tert-butyl (4R)-3-{2-[3-(3-methylphenyl)-ureido]acetyl}-2-butyl-4-thiazolidinecarboxylate (isomer A) is thereby obtained in the form of an amorphous product; $[\alpha]_D^{25}=-39°\pm1°$ (C %=0.53; DMF).

NMR (200 MHz, δ in ppm, DMSO-$d_6$+2 drops of CD$_3$COOD, 373K). 0.90 (t, 3H: CH$_3$), 1.38 (mt, 4H: —CH$_2$—CH$_2$—CH$_3$), 1.50 [s, 9H: —COOC(CH$_3$)$_3$], from 1.50 to 2.15 (mt, 2H: —CH$_2$—), 2.30 (s, 3H: Ar—CH$_3$), from 3.15 to 3.50 (mt, 2H: —S—CH$_2$—), from 3.90 to 4.10 (mt, 2H: N—CH$_2$—CO—), 4.95 (t, 1H: —CH—CO—), 5.30 (dd, 1H: N—CH—S—), 6.25 (residual unres.comp.: —NH—CO—), 6.75 [broad d, 1H: Ar (-H 4)], 7.10 [t, 1H: Ar (-H5)], from 7.15 to 7.25 [mt, 2H: Ar (-H 2 and -H 6 )].

EXAMPLE 13

The procedure is similar to that described in Example 1, but starting with 1.18 g of benzyl (4R)-3-{3-[2-(4-tert-butoxycarbonyl-2-butyl-3-thiazolidinyl)-2-oxoethyl] ureido}benzoate (isomer A), 0.8 g of ammonium formate and 1.2 g of palladium on charcoal (10% Pd). 0.25 g of (4R) -3-{3- [2- (4-tert-butoxycarbonyl-2-butyl-3-thiazolidinyl)-2-oxoethyl]ureido}benzoic acid (isomer A) is thereby obtained in the form of an amorphous products $[\alpha]_D^{25}=-35.4°\pm1.0°$ (C %=0.52; DMF).

NMR (200 MHz, δ in ppm, DMSO-$d_6$+2 drops of CD$_3$COOD, 373K). 0.92 (t, 3H: CH$_3$), 1.40 (mt, 4H:

—CH$_2$—CH$_2$—CH$_3$), 1.52 [s, 9H: —COOC(CH$_3$)$_3$], from 1.50 to 2.15 (mt, 2H: —CH$_2$—), from 3.20 to 3.50 (mt, 2H: —S—CH$_2$—), from 3.90 to 4.10 (mt, 2H: N—CH$_2$—CO—), 4.95 (t, 1H: —N—CH—CO—), 5.32 (dd, 1H: N—CH—S—), 6.30 (residual unres.comp.: —NH—CO—), 7.35 [t, 1H: Ar (-H 5)], 7.52 and 7.62 (2 broad d, 1H each: Ar (-H 4 and -H 6)], 8.05 (broad s, 1H: Ar (-H 2)], 8.70 (residual unres.comp.: Ar—NH—CO—).

A Benzyl (4R)-3-{3-[2-(4-tert-butoxycarbonyl-2-butyl-3-thiazolidinyl)-2-oxoethyl]ureido}benzoate (isomer A) may be prepared in a manner similar to that described in Example 1A, but starting with 2.4 g of tert-butyl (4R)-3-(2-aminoacetyl)-2-butyl-4-thiazolidinecarboxylate (isomer A) and 2.3 g of benzyl 3-isocyanatobenzoate. The crude product obtained is purified by chromatography on silica [eluent: diisopropyl ether/ethyl acetate (95:5 by volume)]. The fractions containing the expected product are pooled and concentrated to dryness under reduced pressure at 40° C. 1.6 g of benzyl (4R)-3-{3-[2-(4-tert-butoxycarbonyl-2-butyl-3-thiazolidinyl)-2-oxoethyl]ureido}benzoate (isomer A) are thereby obtained in the form of an amorphous product, which is used in the subsequent syntheses without further treatment.

EXAMPLE 14

The procedure is similar to that described in Example 1A, but starting with 2.51 g of tert-butyl (2R,4R)-3-(2-aminoacetyl)-2-((RS)-1,2,3,6-tetrahydro-1-phenyl)-4-thiazolidinecarboxylate and 1.06 g of 3-methylphenyl isocyanate. The crude product obtained is purified by chromatography on silica [eluent: methylene chloride/ethyl acetate (90:10 by volume)]. The fractions containing the expected product are pooled and concentrated to dryness under reduced pressure at 40° C. 1.74 g of tert-butyl (2R,4R)-3-{2-[3-(3-methylphenyl) ureido]acetyl}-2- ((RS)-1,2,3,6-tetrahydro-1-phenyl)-4-thiazolidinecarboxylate are thereby obtained in the form of an amorphous product.

NMR (250 MHz, δ in ppm, DMSO-d$_6$, 350K). A 50:50 mixture of the two diastereoisomers is observed; from 1.10 to 1.50 and from 1.80 to 2.30 (mt, 7H: CH— and —CH$_2$— of 1,2,5,6-tetrahydrophenyl), 1.47 and 1.49 [2s, 9H in total: —COOC(CH$_3$)$_3$], 2.25 (s, 3H: —Ar—CH$_3$), from 3.25 to 3.45 (mt, 2H: —S—CH$_2$—), 4.08 (mt, 2H: N—CH$_2$—CO—), 5.00 (broad t, 1H: N—CH—CO—), 5.30 (mt, 1H: N—CH—S—), 5.66 (mt, 2H: —CH=CH— of 1,2,5,6-tetrahydrophenyl), 6.75 [broad d, 1H: Ar (-H 4)], 7.10 [t, 1H: Ar (-H 5)], from 7.15 to 7.25 [mt, 2H: Ar (-H 2 and -H 6)].

EXAMPLE 15

The procedure is similar to that described in Example 1, but starting with 1.36 g of benzyl (2R,4R)-3-[3-{2-[4-tert-butoxycarbonyl-2-(2-phenylphenyl)-3-thiazolidinyl]-2-oxoethyl}ureido]phenylacetate, 0.44 g of ammonium formate and 0.6 g of palladium on charcoal (10% Pd). 0.25 g of (2R,4R)-3-[3-{2-[4-tert-butoxycarbonyl-2-(2-phenylphenyl)-3-thiazolidinyl]-2-oxoethyl}ureido] phenylacetic acid, melting point 128° C., is thereby obtained; [α]$_D^{25}$=-26.2°±0.9° (C %=0.56; MeOH).

NMR (200 MHz, δ in ppm, DMSO-d$_6$+2 drops of CD$_3$COOD, 393K). 1.60 [s, 9H: —COOC(CH$_3$)$_3$], 3.30 and 3.38 (2dd, 1H each: —CH$_2$—S—), 3.49 (s, 2H: Ar—CH$_2$—COO—), from 3.60 to 3.75 and 3.86 (unres.comp. and d, respectively, 1H each: N—CH$_2$—CO—), 4.95 (dd, 1H: N—CH—COO—), 6.08 (s, 1H: N—CH—S—), 6.14 (residual unres.comp.: —CO—NH—), 6.85 [d, 1H: Ar (-H 4)], 7.15 [t, 1H: Ar (-H 5)], from 7.20 to 7.35 [mt, 2H: Ar (-H 2 and -H 6)], from 7.20 to 7.60 and 8.09 (mt and broad d, respectively, 8H and 1H: aromatic -H), 8.40 (residual broad s: —CO—NH—Ar).

A Benzyl (2R,4R)-3-[3-{2-[4-tert-butoxycarbonyl-2-(2-phenylphenyl)-3-thiazolidinyl]-2-oxoethyl}ureido]-phenylacetate may be prepared in a manner similar to that described in Example 1A, but starting with 2.64 g of tert-butyl (2R,4R)-3-(2-aminoacetyl)-2-(2-phenylphenyl)-4-thiazolidinecarboxylate and 3.54 g of benzyl 3-isocyanatophenylacetate. The crude product obtained is purified by chromatography on silica [eluent: methylene chloride/ethyl acetate (90:10 by volume)]. The fractions containing the expected product are pooled and concentrated to dryness under reduced pressure at 40° C. 0.87 g of benzyl (2R,4R)-3-[3-{2-[4-tert-butoxycarbonyl-2-(2-phenylphenyl)-3-thiazolidinyl]-2-oxoethyl}ureido] phenylacetate is thereby obtained in the form of An amorphous product, which is used in the subsequent syntheses without further treatment.

B tert-Butyl (2R,4R)-3-(2-aminoacetyl)-2-(2-phenylphenyl)-4-thiazolidinecarboxylate may be prepared in a manner similar to that described in Example 1B, but starting with 4.0 g of tert-butyl (2R,4R)-3-(2-tert-butoxycarbonylaminoacetyl)-2-(2-phenylphenyl)-4-thiazolidinecarboxylate and 1.43 cm$^3$ of iodotrimethylsilane. 3.9 g of tert-butyl (2R,4R)-3-(2-aminoacetyl)-2-(2-phenylphenyl)-4-thiazolidinecarboxylate are thereby obtained in the form of a yellow oil, which is used in the subsequent syntheses without further treatment.

C tert-Butyl (2R,4R)-3-(2-tert-butoxycarbonyl-aminoacetyl)-2-(2-phenylphenyl)-4-thiazolidinecarboxylate may be prepared in a manner similar to that described in Example 1C, but starting with 5.44 g of tert-butyl (2RS,4R)-2-(2-phenylphenyl)-4-thiazolidinecarboxylate, 2.8 g of 2-tert-butoxycarbonylaminoacetic acid and 3.3 g of N,N'-dicyclohexylcarbodiimide. The crude product is purified by chromatography on silica [eluent: cyclohexane/ethyl acetate (80:20 by volume)]. The fractions containing the expected product are pooled and concentrated to dryness under reduced pressure at 40° C. 4.42 g of tert-butyl (2R,4R)-3-(2-tert-butoxycarbonylaminoacetyl)-2-(2-phenylphenyl)-4-thiazolidinecarboxylate are thereby obtained in the form of a white foam, which is used in the subsequent syntheses without further treatment.

D tert-Butyl (2RS,4R)-2-(2-phenylphenyl)-4-thiazolidinecarboxylate may be prepared in a manner similar to that described in Example 1D, but starting with 6.0 g of (2RS,4R)-2-(2-phenylphenyl)-4-thiazolidinecarboxylic acid suspended in 100 cm$^3$ of chloroform, 3 cm$^3$ of concentrated sulphuric acid and an excess of isobutene. The crude product is purified by chromatography on silica [eluent: cyclohexane/ethyl acetate (80:20 by volume)]. The fractions containing the expected product are pooled and concentrated to dryness under reduced pressure at 40° C. 6.1 g of tert-butyl (2RS,4R)-2-(2-phenylphenyl)-4-thiazolidinecarboxylate are thereby obtained in the form of a yellow oil, which is used in the subsequent syntheses without further treatment.

E (2RS,4R)-2-(2-Phenylphenyl)-4-thiazolidinecarboxylic acid may be prepared in a manner similar to that described in Example 1E, but starting with 5.0 g of L-cysteine and 7.8 g of 2-phenylbenzaldehyde. 8.5 g of (2RS,4R)-2-(2-phenylphenyl)-4-thiazolidinecarboxylic acid, melting point 190° C., are thereby obtained.

F 2-Phenylbenzaldehyde may be prepared in the following manner: 2.5 g of tetrakis(triphenylphosphine)-palladium(O) and 40 cm$^3$ of 2M aqueous sodium carbonate solution are added to a solution containing 8.0 g of 2-bromobenzaldehyde and 5.2 g of phenylboronic acid in 80 cm³ of dimethoxyethane. The reaction medium is heated to reflux for 12 hours and then, after return to a temperature in the vicinity of 25° C., diluted with 200 cm³ of ethyl acetate. The organic phase is separated after settling has taken place, washed with twice 50 cm³ of water, dried over magnesium sulphate and concentrated to dryness under reduced pressure at 40° C. The crude product obtained is purified by chromatography on silica [eluent: cyclohexane/ethyl acetate (95:5 by volume)]. The fractions containing the expected product are pooled and concentrated to dryness under reduced pressure at 40° C. 8.1 g of 2-phenylbenzaldehyde are thereby obtained in the form of a yellow oil, which is used in the subsequent syntheses without further treatment.

EXAMPLE 16

The procedure is similar to that described in Example 1A, but starting with 1.32 g of tert-butyl (2R,4R)-3-(2-aminoacetyl)-2-(2-phenylphenyl)-4-thiazolidinecarboxylate and 0.47 g of 3-methylphenyl isocyanate. The crude product is purified by chromatography on silica [eluent: methylene chloride/ethyl acetate (90:10 by volume)]. The fractions containing the expected product are pooled and concentrated to dryness under reduced pressure at 40° C. After vigorous stirring in pentane, 0.22 g of tert-butyl (2R,4R)-3-{2-[3-(3-methylphenyl)-ureido]acetyl}-2-(2-phenylphenyl)-4-thiazolidinecarboxylate is thereby obtained in the form of an amorphous product; $[\alpha]_D^{25}=-9.8\pm0.9°$ (C %=0.49; CHCl₃).

NMR (300 MHz, δ in ppm, DMSO-d₆+2 drops of CD₃COOD, 393K). A mixture of the two rotamers (50:50) is observed: 1.50 and 1.60 [2s, 9H in total: —COOC(CH₃)₃], 2.24 (s, 3H, Ar—CH₃), from 3.10 to 4.10 (mt, 4H: —CH₂—S—and N—CH₂—CO—), 4.67 and 5.19 (t and dd, respectively, 1H in total: N—CH—COO—), 5.98 and 6.00 (2s, 1H: N—CH—S—), 6.22 and 6.31 (2t, 1H in total: —NH—CO—), 6.73 [d, 1H: Ar (-H 4)], from 7.05 to 7.20 [mt, 3H: Ar (-H2, -H5 and -H6)], from 7.20 to 7.60–7.91 and 8.25 (mt and 2 broad d, respectively, 8H -1H: aromatic -H), 8.62 and 8.71 (2 broad s, 1H in total: —CO—NH—Ar).

EXAMPLE 17

12.4 cm³ of 0.1N aqueous sodium hydroxide solution are added to a solution of 0.22 g of (S)-3-[3-{2-[(2R, 4R)-4-tert-butoxycarbonyl-1-2- (2-fluorophenyl)-3-thiazolidinyl]-2-oxoethyl}ureido]-2-phenylpropionic acid in 10 cm³ of tetrahydrofuran. The reaction medium is stirred for 48 hours at a temperature in the region of 25° C., and the organic solvent is then removed evaporation under reduced pressure. The aqueous solution obtained is filtered and brought to a pH in the region of 3 by adding 1N aqueous sulphuric acid solution. The precipitate obtained is separated filtration, washed with twice 5 cm³ of distilled water and dried in the air. 0.15 g of (S)-3-[[3-{2-[(2R,4RS)- 4-carboxy-1-2-(2-fluorophenyl)-3-thiazolidinyl]-2-oxoethyl}ureido]-2-phenylpropionic acid, melting point 148° C., is thereby obtained.

NMR (300 MHz, δ in ppm, DMSO-d₆+2 drops of CD₃COOD, 393K). A mixture of the two diastereoisomers (65:35) is observed: 1.38 (d, 3H; —CH₃), from 3.25 to 3.60 (mt, 2H: —S—CH₂—), 3.58 (q, 1H: Ar—CH—COO—), 3.77 and 4.09 (mt and 2d, respectively, 1H each: N—CH₂—CO—), 5.05 and 5.34 (t and dd, respectively, 1H in total: N—CH—CO—), 6.38 and 6.54 (2s, 1H in total: N—CH—S—), 6.85 [broad d, 1H: Ar (-H 4)], from 7.10 to 8.00 [mt, 7H: Ar (-H 5, -H2 and -H6 and aromatic)].

(S) -3- [3-{2- [(2R, 4R) -4-tert-Butoxycarbonyl-1-2-(2-fluorophenyl)-3-thiazolidinyl]-2-oxoethyl}ureido]-2-phenylpropionic acid may be prepared according to the method described in Patent WO 93/01,165.

The medicinal products according to the invention consist of a compound of formula (I), in free form or in the form of a salt, in the pure state or in the form of a composition in which it is combined with any other pharmaceutically compatible product, which may be inert or physiologically active. The medicinal products according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, for example one or more lubricants such as magnesium stearate or talc, a colouring, a coating (dragée) or a varnish.

As liquid compositions for oral administration, pharmaceutically acceptable solutions, suspensions, emulsions, syrups and elixirs may be used, containing inert diluents such as water, ethanol, glycerol, vegetable oils or liquid paraffin. These compositions can comprise substances other than diluents, for example wetting, sweetening, thickening, flavouring or stabilizing products.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, tonicity, emulsifying, dispersing and stabilizing agents. The sterilization may be carried out in several ways, for example by aseptic filtration, by incorporating sterilizing agents in the composition, by irradiation or by heating. They may also be prepared in the form of sterile solid compositions which can be dissolved at the time of use in sterile water or any other sterile injectable medium.

The compositions for rectal administration are suppositories or rectal capsules which contain, apart from the active product, excipients such as cocoa butter, semi-synthetic glycerides or polyethylene glycols.

The compositions for topical administration can be, for example, creams, lotions, eyewashes, mouthwashes, nasal drops or aerosols.

In human therapy, the compounds according to the invention are especially useful in the treatment and prevention of disorders linked to CCK and to gastrin affecting the nervous system and the gastrointestinal system. These compounds may hence be used in the treatment and prevention of psychoses, anxiety disorders, depression, neurodegeneration, panic attacks, Parkinson's disease, tardive dyskinesia, irritable colon syndrome, acute pancreatitis, ulcers, disorders of intestinal motility, certain CCK-sensitive rumours and memory disorders, in the withdrawal of chronic treatments and abuse of alcohol or of medicinal products, as constrictors of the pupil of the eye, as analgesics, as potentiators of the analgesic activity of narcotic and non-narcotic analgesic medicinal products and as appetite regulators.

The doses depend on the effect sought, the duration of the treatment and the administration route used; they are generally between 0.05 g and 1 g per day via the oral route for an adult, with single doses ranging from 10 mg to 500 mg of active substance.

Generally speaking, the doctor will determine the appropriate dosage in accordance with the age, weight and all other factors specific to the subject who is to be treated.

The examples which follow illustrate compositions according to the invention:

EXAMPLE A Hard gelatin capsules containing a 50 mg dose of active product and having the following composition are prepared according to the usual technique:

(4R)-3-{3-[2-(4-tert-Butoxycarbonyl-2-cyclohexyl-3-thiazolidinyl)-2-oxoethyl]ureido}-phenylacetic acid (isomer A) 50 mg Cellulose 18 mg Lactose 55 mg Colloidal silica 1 mg Sodium carboxymethyl starch 10 mg Talc 10 mg Magnesium stearate 1 mg EXAMPLE B Tablets containing a 50 mg dose of active product and having the following composition are prepared according to the usual technique:

tert-Butyl (4R)-3-{2-[3-(3-methylphenyl)ureido]acetyl}-2-benzyl-4-thiazolidinecarboxylate (isomer A) 50 mg Lactose 104 mg Cellulose 40 mg Povidone 10 mg Sodium carboxymethyl starch 22 mg Talc 10 mg Magnesium stearate 2 mg Colloidal silica 2 mg Mixture of hydroxymethylcellulose, glycerol and titanium oxide (72:3.5:24.5) g.s. I finished film-coated tablet weighing 245 mg EXAMPLE C An injection containing 10 mg of active product and having the following composition is prepared:

(4R)-3-{3-[2-(4-tert-Butoxycarbonyl-2-benzyl-3-thiazolidinyl)-2-oxoethyl]ureido}phenylacetic acid (isomer A) 10 mg Benzoic acid 80 mg Benzyl alcohol 0.06 cm$^3$ Sodium benzoate 80 mg Ethanol, 95% 0.4 cm$^3$ Sodium hydroxide 24 mg Propylene glycol 1.6 cm$^3$ Water q.s. 4 cm$^3$ Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

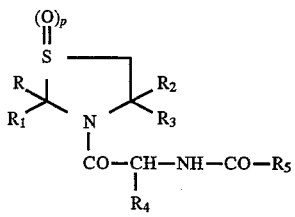

(I)

in which

R represents an unbranched- or branched-chain alkyl radical containing 1 to 12 carbon atoms and optionally mono- or polyunsaturated, a cycloalkyl radical containing 3 to 12 carbon atoms and optionally mono- or polyunsaturated, a polycycloalkyl radical containing 6 to 12 carbon atoms and optionally mono- or polyunsaturated, a phenylalkyl radical in which the phenyl ring is optionally substituted with at least one substituent selected from alkyl and alkoxy radicals or halogen atoms, a diphenylalkyl or cinnamyl radical, a pyridyl radical optionally substituted with at least one alkyl radical, a furyl radical optionally substituted with at least one alkyl radical, a thienyl radical optionally substituted with one or more alkyl radicals, a quinolyl radical optionally substituted with at least one alkyl radical, a naphthyl radical optionally substituted with at least one alkyl radical, an indolyl radical optionally substituted with at least one alkyl radical, a 2-oxopiperidyl or quinuclidinyl radical or a phenyl radical optionally substituted with at least one substituent selected from halogen atoms and alkyl, alkoxy, hydroxyl, nitro, amine, monoalkylamino, dialkylamino, alkoxycarbonyl, —CO—NR$_7$R$_8$, —NH—CO—CH$_3$, trifluromethyl, phenyl or trifluoromethoxy radicals, R$_1$ represents an hydrogen atom, an alkyl, cycloalkyl or phenylalkyl radical or a phenyl radical optionally substituted with at least one substituent selected from halogen atoms and alkyl and alkoxy radicals, R$_2$ represents a chain —(CH$_2$)$_n$—CO—R$_6$, —(CH$_2$)$_m$—O—CO—R"$_6$ or —(CH$_2$)$_m$—NR$_9$R$_{10}$, an oxazolinyl radical optionally substituted with at least one alkyl radical or a 3-alkyloxadiazolyl radical, R$_3$ represents a hydrogen atom, an alkyl, cycloalkyl or phenylalkyl radical or a phenyl radical optionally substituted with at least one substituent selected from halogen atoms and alkyl and alkoxy radicals, R$_4$ represents a hydrogen atom or an alkyl radical, R$_5$ represents a phenyl radical optionally substituted with at least one substituent selected from halogen atoms and alkyl, alkoxy and alkylthio radicals, a naphthyl, indolyl or quinolyl radical or a phenylamino radical in which the phenyl ring is optionally substituted with at least one substituent selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, —alk—O—CO—alk, —alk—COOX, —alk—O—alk, —alk'—COOX, —O—alk—COOX, —CH=CH—COOX, —CO—COOX, —alk—SO$_3$H (in salt form), —CH=CH—alk', —C(=NOH)—COOX, —S—alk—COOX, —SO—alk—COOX, —SO$_2$—alk—COOX, —O—CH$_2$—alk'—COOX, —CX=N—O—alk—COOX, —alk—N(OH)—CO—alk, —alk—SO$_2$H, —SO$_2$—NH—CO—R$_{11}$, —SO$_2$—NH—SO—R$_{11}$, —CO—NH—CO—R$_{11}$, —CO—NH—SO$_2$—

$R_{11}$, —B(OH)$_2$, —C(NH$_2$)=NOH, —SO$_2$—NH—$R_{12}$, —CO—NH—$R_{12}$,

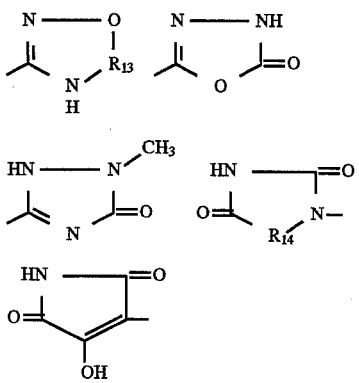

or 2,2-dimethyl-4,6-dioxo-1,3-dioxan-5-yl radicals,

R6 represents a hydroxyl, alkoxy, cycloalkyloxy, cycloalkylalkyloxy or phenyl radical or a radical —NR$_9$R$_{10}$, R"$_6$ represents an alkoxy, cycloalkyloxy, cycloalkylalkyloxy or phenyl radical or a radical —NR$_9$R$_{10}$, R$_7$ represents a hydrogen atom, an alkyl or phenylalkyl radical or a phenyl radical optionally substituted with at least one substituent selected from halogen atoms and alkyl, alkoxy and alkylthio radicals, R$_8$ represents an alkyl or phenylalkyl radical or a phenyl radical optionally substituted with at least one substituent selected from halogen atoms and alkyl, alkoxy and alkylthio radicals, or alternatively R$_7$ and R$_8$, with the nitrogen atom to which they are attached, form a saturated or unsaturated mono- or polycyclic heterocycle containing 4 to 9 carbon atoms and at least one hetero atom including O or N and optionally substituted with at least one alkyl radical, R$_9$ represents a hydrogen atom, an alkyl, cycloalkylalkyl, cycloalkyl or phenylalkyl radical or a phenyl radical optionally substituted with at least one substituent selected from halogen atoms and alkyl, alkoxy and alkylthio radicals, R$_{10}$, represents an alkyl, cycloalkylalkyl, cycloalkyl or phenylalkyl radical or a phenyl radical optionally substituted with at least one substituent selected from halogen atoms and alkyl, alkoxy and alkylthio radicals, or alternatively R$_9$ and R$_{10}$, together with the nitrogen atom to which they are attached, form a saturated or unsaturated mono- or polycyclic heterocycle containing 4 to 9 carbon atoms and at least one hetero atom including O, N or S and optionally substituted with at least one alkyl radical, R$_{11}$ represents an alkyl, cycloalkyl or trifluoromethyl radical or a phenyl radical optionally substituted with at least one substituent selected from cyano, alkoxy, nitro and amino radicals and halogen atoms, R$_{12}$ represents a 5-tetrazolyl radical, R$_{13}$ represents C=O or S=O, R$_{14}$ represents O or C=O, p is equal to 0, 1 or 2, n is equal to 0, 1 or 2, m is equal to 1 or 2, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical, n is other than 0 when R$_1$ and R$_3$ each represent a hydrogen atom and R represents a pyridyl radical optionally substituted with at least one alkyl radical, a furyl radical optionally substituted with at least one alkyl radical, a thienyl radical optionally substituted with at least one alkyl radical, a quinolyl radical optionally substituted with at least one alkyl radical, a naphthyl radical optionally substituted with at least one alkyl radical, an indolyl radical optionally substituted with at least one alkyl radical or a phenyl radical optionally substituted with at least one substituent selected from halogen atoms and alkyl, alkoxy, hydroxyl, nitro, amino, monoalkylamino, dialkylamino, alkoxycarbonyl, —CO—NR$_7$R$_8$, —NH—CO—CH], trifluoromethyl or trifluoromethoxy radicals, and except where otherwise stated, the alkyl, alkylene and alkoxy radicals and the alkyl, alkylene and alkoxy portions contain 1 to 4 carbon atoms in an unbranched or branched chain, the acyl radicals and portions contain 2 to 4 carbon atoms and the cycloalkyl radicals and portions contain 3 to 6 carbon atoms, a salt thereof or an isomer thereof when said compound contains at least one asymmetric center.

2. A compound of formula (I) according to claim 1 for which R represents an isopropenyl, cyclohexyl, tetrahydrophenyl, cyclopentadiene, dihydrophenyl, norbornyl, adamantyl or norbornenyl radical, a salt thereof or an isomer thereof when said compound contains at least one asymmetric center.

3. A compound of formula (I) according to claim 1 wherein R$_7$ and R$_8$, with the nitrogen atom to which they are attached, form a heterocycle selected from a piperidino ring optionally substituted with at least one alkyl radical and a 1,2,3,4-tetrahydroquinoline ring-system, a salt thereof or an isomer thereof when said compound contains at least one asymmetric center.

4. A compound of formula (I) according to claim 1 wherein R$_9$ and R$_{10}$, with the nitrogen atom to which they are attached, form a heterocycle selected from piperidino, perhydro-1-azepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino and 1-indolinyl ring-systems, these ring-systems optionally substituted with at least one alkyl radical, a salt thereof or an isomer thereof when said compound contains at least one asymmetric center.

5. A compound of formula (I) according to claim 1 wherein R represents an unbranched- or branched-chain alkyl radical containing 1 to 12 carbon atoms, a cycloalkyl radical containing 3 to 12 carbon atoms and optionally monounsaturated, a polycyloalkyl radical containing 6 to 12 carbon atoms and optionally mono- or polyunsaturated, a phenylalkyl radical or a phenyl radical optionally substituted with at least one substituent selected from halogen atoms and alkyl, —alk—COOX and carboxyl radicals, R$_1$ represents a hydrogen atom, R$_2$ represents a chain —(CH$_2$)$_n$—CO—R$_6$, R$_3$ represents a hydrogen atom, R$_4$ represents a hydrogen atom and R$_5$ represents a phenylamino radical in which the phenyl ring is substituted with an alkyl, —alk—COOX or carboxyl radical, or a salt thereof or an isomer thereof when said compound contains at least one asymmetric center.

6. A compound selected from the group consisting of:
(4R)-3-{3-[2-(4-tert-Butoxycarbonyl-2-cyclohexyl-3-thiazolidinyl)-2-oxo ethyl]ureido}phenylacetic acid,
tert-Butyl (4R)-3-{2-[3-(3-methylphenyl)ureido]-acetyl}-2-benzyl-4-thiazolidinecarboxylate,
(4R)-3-{3-[2-(4-tert-Butoxycarbonyl-2-benzyl-3-thiazolidinyl)-2-oxoethyl]ureido}phenylacetic acid,
(2R,4R)-3-[3-{2-[4-tert-Butoxycarbonol-2-((RS)-1,2,3,6-tetrahydro-1-phenyl)-3-thiazolidinyl]-2-oxoethyl}ureido] phenylacetic acid,
(4R)-3-[3-{2-[4-tert-Butoxycarbonyl-2-[(2RS)-5-norbornen-2-yl]-3-thiazolidinyl]-2-oxoethyl}ureido]-phenylacetic acid, Methyl (4R)-3-[3-{2-[4-tert-butoxycarbonyl-2-[(2RS)-5-norbornen-2-yl]-3-thiazolidinyl]-2-oxoethyl}ureido]-phenylacetate, (4R)-3-[3-{2-[4-tert-Butoxycarbonyl-2-[(2RS)-5-norbornen-2-yl]-3-thiazolidinyl]-2-oxoethyl}ureido]-phenylacetic acid, (4R)-3-[3-{2-[4-tert-Butoxycarbonyl-2-((2RS)-2-norbornyl)-3-thiazolidinyl]-2-oxoethyl}-ureido]-phenylacetic acid, tert-Butyl (4R)-3-{2-[3-(3-methylphenyl)ureido]-acetyl}-2-[(RS)-5-norbornen-2-yl]thiazolidine-carboxylate, (4R)-3-{3-2-(4-tert-Butoxycarbonyl-2-tert-butyl-3-thiazolidinyl)-2-oxoethyl]ureido}phenylacetic acid, (S)-3-{3-[2-((4R)-4-tert-butoxycarbonyl-2-butyl-3-thiazolidinyl)-2-oxoethyl]ureido}-2-phenylpropionic acid, tert-Butyl (4R)-3-{2-[3-(3-methylphenyl)ureido]-acetyl}-2-butyl-4-thiazolidinecarboxylate, (4R)-3-{3-[2-(4-tert-Butoxycarbonyl-2-butyl-3-thiazolidinyl)-2-oxoethyl]ureido}benzoic acid, tert-Butyl (2R,4R)-3-{2-[3-(3-methylphenyl)ureido]-acetyl}-2-((RS)-1,2,3,6-tetrahydro-1-phenyl)-4-thiazolidinecarboxylate, (2R,4R)-3-[3-{2-[4-tert-Butoxycarbonyl-2-(2-phenylphenyl)-3-thiazolidinyl]-2-oxoethyl}ureido]-phenylacetic acid, tert-Butyl (2R,4R)-3-{2-[3-(3-methylphenyl)ureido]-acetyl}-2-(2-phenylphenyl)-4-thiazolidinecarboxylate, (S)-3-[[3-{2-[(2R,4RS)-4-Carboxy-2-(2-fluorophenyl)-3-thiazolidinyl]-2-oxoethyl}ureido]-2-phenylpropionic acid, an isomer thereof, a mixture of said isomers or a salt thereof.

7. A pharmaceutical composition comprising an effective amount of at least one compound according to claim 1 and a pharmaceutically acceptable carrier.

8. A method for antagonizing cholecystokinin or gastrin in a mammal having a disorder linked to cholecystokinin or to gastrin at the level of the nervous system or of the gastrointestinal tract, comprising administering to a mammal in need of such treatment an effective amount of at least one compound according to claim 1.

* * * * *

UNITED STATES PATENT AND TRADEMARK OFFICE
CERTIFICATE OF CORRECTION

PATENT NO. : 5,633,270
DATED : May 27, 1997
INVENTOR(S): Marie-Christine DUBROEUCQ et al.

It is certified that error appears in the above-identified patent and that said Letters Patent is hereby corrected as shown below:

Title Page, Item [54], third line of title, "SAMEM" should read --THEM--.

Claim 1, column 36, line 32, "amine" should read --amino--.

Claim 1, column 37, line 20, R6represents" should read --$R_6$ represents--;

Claim 1, column 37, line 41, delete "," after "$R_{10}$".

Claim 1, column 38, line 10, "-NH-CO-CH]," should read --$NH-CO-CH_3$,--.

Signed and Sealed this

Third Day of March, 1998

BRUCE LEHMAN

*Attest:*

*Attesting Officer*  Commissioner of Patents and Trademarks